US012558136B2

(12) United States Patent
Vogt et al.

(10) Patent No.: US 12,558,136 B2
(45) Date of Patent: Feb. 24, 2026

(54) APPARATUS FOR PROVIDING A LIQUID COMPONENT OF A BONE CEMENT DOUGH, SYSTEM AND METHOD FOR PROVIDING A BONE CEMENT DOUGH

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 628 days.

(21) Appl. No.: 18/048,083

(22) Filed: Oct. 20, 2022

(65) Prior Publication Data

US 2023/0127890 A1 Apr. 27, 2023

(30) Foreign Application Priority Data

Oct. 25, 2021 (EP) ...................................... 21204369

(51) Int. Cl.
*A61B 17/88* (2006.01)
*B01F 23/50* (2022.01)
(Continued)

(52) U.S. Cl.
CPC .......... *A61B 17/8833* (2013.01); *B01F 23/54* (2022.01); *B01F 23/59* (2022.01);
(Continued)

(58) Field of Classification Search
CPC .............. B01F 35/7174; B01F 35/7131; B01F 2101/20; A61B 17/8833; A61B 17/8838
See application file for complete search history.

(56) References Cited

U.S. PATENT DOCUMENTS 6,709,149 B1 * 3/2004 Tepic ................... B01F 35/7164
366/139
8,287,641 B2 10/2012 Bohner
(Continued)

FOREIGN PATENT DOCUMENTS

EP 1592463 B1 8/2006
EP 3150155 A1 4/2017
(Continued)

OTHER PUBLICATIONS

Charnley, Anchorage of the femoral head prosthesis of the shaft of the femur, The Journal of Bone and Joint Surgery, vol. 42-B, No. 1 (1960), pp. 28-30, Feb. 1, 1960.

*Primary Examiner* — Marc C Howell
(74) *Attorney, Agent, or Firm* — Dicke, Billig & Czaja, PLLC

(57) ABSTRACT

An apparatus for providing a liquid component as a first starting component of a bone cement dough from two starting components, comprising a receptacle in which a tank containing the liquid component can be stored, an opening means for opening the tank, a reservoir, fluidically connected to the receptacle, for receiving the liquid component from the tank, at least one port for fluidically connecting the apparatus to a syringe in which a powder component can be stored as a second starting component of the bone cement dough, and at least one conducting means which fluidically connects the reservoir and the at least one port to one another.

14 Claims, 13 Drawing Sheets

(51) Int. Cl.
    *B01F 35/71*          (2022.01)
    *B01F 101/20*       (2022.01)

(52) U.S. Cl.
    CPC ........ *B01F 35/715* (2022.01); *B01F 35/7174*
    (2022.01); *A61B 2017/8838* (2013.01); *B01F*
    *35/7131* (2022.01); *B01F 2101/20* (2022.01);
    *B01F 2215/0431* (2013.01)

(56) References Cited

U.S. PATENT DOCUMENTS

| | | | |
|---|---|---|---|
| 8,303,599 | B2 | 11/2012 | Hess et al. |
| 8,348,494 | B2 | 1/2013 | Melsheimer et al. |
| 9,131,930 | B2 | 9/2015 | Greter |
| 9,611,173 | B2 | 4/2017 | Doebelin et al. |
| 9,642,932 | B2 | 5/2017 | Beyar et al. |
| 9,707,314 | B2 | 7/2017 | DiMauro |
| 10,307,195 | B2 | 6/2019 | Vog |
| 2006/0041033 | A1 | 2/2006 | Bisig et al. |
| 2006/0273109 | A1 | 12/2006 | Keller |
| 2006/0274601 | A1 | 12/2006 | Seaton, Jr. |
| 2010/0054075 | A1 | 3/2010 | Valaie |
| 2010/0329074 | A1* | 12/2010 | Vogt .................. B01F 35/71805 |
| | | | 366/190 |
| 2011/0273954 | A1* | 11/2011 | Greter ................. B01F 35/2113 |
| | | | 366/142 |
| 2012/0132675 | A1* | 5/2012 | Vogt .................... B01F 33/5011 |
| | | | 222/386 |
| 2019/0038331 | A1 | 2/2019 | Purdy et al. |

FOREIGN PATENT DOCUMENTS

| | | |
|---|---|---|
| EP | 2271585 B1 | 3/2018 |
| EP | 2988789 B1 | 5/2018 |
| EP | 3122391 B1 | 5/2019 |
| WO | 2005018831 A1 | 3/2005 |
| WO | 2005123162 A1 | 12/2005 |
| WO | 2006132779 A2 | 12/2006 |
| WO | 2008032322 A3 | 5/2009 |
| WO | 2010145041 A1 | 12/2010 |

* cited by examiner

APPARATUS FOR PROVIDING A LIQUID COMPONENT OF A BONE CEMENT DOUGH, SYSTEM AND METHOD FOR PROVIDING A BONE CEMENT DOUGH

CROSS-REFERENCE TO RELATED APPLICATIONS

This application claims priority pursuant to 35 U.S.C. 119(a) to European Application No. 21204369.9, filed Oct. 25, 2021, which application is incorporated herein by reference in its entirety.

FIELD

The invention relates to an apparatus for providing a liquid component as a first starting component of a bone cement dough from two starting components, comprising a receptacle in which a tank containing the liquid component can be stored, an opening means for opening the tank, a reservoir, fluidically connected to the receptacle, for receiving the liquid component from the tank, at least one port for fluidically connecting the apparatus to a syringe in which a powder component can be stored as a second starting component of the bone cement dough, and at least one conducting means which fluidically connects the reservoir and the at least one port to one another.

The invention furthermore relates to a system for providing a bone cement dough from two starting components, comprising such an apparatus, a tank containing a liquid component as the first starting component, and a plurality of syringes, each containing a powder component as the second starting component, and to a method for providing a bone cement dough from two starting components by means of such a system.

BACKGROUND OF THE INVENTION

A frequently used procedure for treating vertebral body fractures is vertebroplasty. In this process, a fractured vertebral body is stabilized with a bone cement, for example a polymethyl methacrylate bone cement or an inorganic bone cement, which, for this purpose, is introduced into the vertebral body in the liquid to viscous state as bone cement dough and cures therein to form the bone cement.

Bone cement dough is usually provided by mixing two starting components, namely a liquid component and a powder component, wherein the curing of the bone cement dough starts with the mixing of the starting components. Within a few minutes, for example within 10 minutes, the bone cement dough provided cures completely to form the bone cement. In order to carry out the vertebroplasty, a surgeon only has a limited time window after the bone cement dough has been provided and before the bone cement dough has exceeded its processing time and can no longer be used as desired.

For reasons relating to surgical technique, in particular due to improved handling, small syringes, for example with a capacity of up to 10 ml, are used in vertebroplasty. Since more bone cement dough than the capacity of one of these small syringes is usually required, a plurality of syringes containing bone cement dough must be provided for a surgery.

Packages for bone cements that are usually purchased in the retail market are sufficient to fill a plurality of the syringes used in vertebroplasty. Mixing a bone cement dough for only one of the syringes in each case and discarding the remainder of the mixed bone cement dough is not sensible for commercial reasons. To date, a large amount of bone cement dough has therefore been provided by means of a single package, for example a single package in the form of a tank for the liquid component and a single bag containing a powder component, which is subsequently divided into a plurality of the syringes.

By way of example, patent specification U.S. Pat. Nos. 8,348,494 B2 is mentioned here, in which a previously provided bone cement dough is distributed into a plurality of syringes for application into a patient's body.

This is disadvantageous in that the processing time of the bone cement dough begins for all syringes simultaneously, namely with the initial mixing of the entire amount of bone cement dough. This puts the surgeon under considerable time pressure since all syringes have to be used within the processing time. Furthermore, this has the consequence that only bone cement doughs having a relatively long processing time can be used if a plurality of syringes filled with bone cement doughs are used, for example in order to stabilize a plurality of vertebral bodies. This restricts the surgeon's choice of available bone cement doughs. At the same time, the rheological properties of the initially mixed bone cement dough divided into the syringes differ. While the bone cement dough used first in the course of the surgery can, for example, still have a comparatively low viscosity, the bone cement dough in the syringe used last has an already significantly higher viscosity. This makes performing the surgery more difficult. If the application of the bone cement dough takes a long time, in particular exceeds the processing time of the initially provided bone cement dough, it may be that one or more of the previously filled syringes can no longer be used. This makes it necessary to again provide a further bone cement dough by means of a further package, for example a further tank containing the liquid component as the starting component of the bone cement dough, which is also disadvantageous from a commercial point of view.

OBJECTS

It is an object of the present invention to at least partially overcome one or more of the disadvantages resulting from the prior art.

In particular, the invention is based on the goal of providing an apparatus which makes it possible to provide a plurality of syringes filled with bone cement dough which can be provided from two starting components, wherein the bone cement dough is intended to be providable for all syringes from a single package comprising a container for a powder component and a tank for a liquid component, without a user of the apparatus having to use all syringes within a period of time corresponding to the processing time of the bone cement dough. The apparatus should also allow the use of bone cement doughs that cure quickly. The apparatus should allow mixing of the bone cement dough directly in the syringes so that the surgeon does not have to transfer the bone cement dough into the syringes.

It is a further object of the invention to provide a system for providing a bone cement dough from two starting components, comprising such an apparatus, by means of which system at least some of the objects already described are achieved at least in part.

A further object of the invention is to provide a method by means of which a bone cement dough can be provided from two starting components, by means of which method at least some of the objects already described are achieved at least in part.

PREFERRED EMBODIMENTS OF THE INVENTION

The features of the independent claims contribute to at least partially fulfilling at least one of the aforementioned objects. The dependent claims provide preferred embodiments which contribute to at least partially fulfilling at least one of the objects.

A first embodiment of the invention is an apparatus for providing a liquid component as a first starting component of a bone cement dough from two starting components, comprising a receptacle in which a tank containing the liquid component can be stored, an opening means for opening the tank, a reservoir, fluidically connected to the receptacle, for receiving the liquid component from the tank, at least one port for fluidically connecting the apparatus to a syringe in which a powder component can be stored as a second starting component of the bone cement dough, and at least one conducting means which fluidically connects the reservoir and the at least one port to one another.

In one embodiment, the apparatus comprises a plurality of ports, in particular two, three, four or five ports, for fluidically connecting the apparatus to a syringe in which a powder component can be stored as the second starting component of the bone cement dough, and a plurality of conducting means, in particular two, three, four or five conducting means, wherein one of the conducting means of the plurality of conducting means in each case fluidically connects the reservoir and one port of the plurality of ports to one another. This embodiment is a second embodiment of the invention which is preferably dependent on the first embodiment of the invention.

In one embodiment of the apparatus, the reservoir is divided into a plurality of compartments, in particular into two, three, four or five compartments, wherein one of the compartments of the plurality of compartments is in each case fluidically connected to one of the ports of the plurality of ports via one of the conducting means of the plurality of conducting means. This embodiment is a third embodiment of the invention which is preferably dependent on the second embodiment of the invention.

In one embodiment of the apparatus, the compartments each have a substantially equal volume. This embodiment is a fourth embodiment of the invention which is preferably dependent on the third embodiment of the invention.

In one embodiment of the apparatus, the reservoir is divided into the compartments by means of at least one partition wall. This embodiment is a fifth embodiment of the invention which is preferably dependent on the third or fourth embodiment of the invention.

In one embodiment of the apparatus, the compartments are in each case fluidically open at an upper compartment side facing the receptacle, so that the compartments are fluidically connected to one another via the upper compartment sides. This embodiment is a sixth embodiment of the invention which is preferably dependent on the fifth embodiment of the invention.

In one embodiment of the apparatus, the at least one conducting means is a tube. This embodiment is a seventh embodiment of the invention which is preferably dependent on one of the preceding embodiments of the invention.

In one embodiment of the apparatus, the tube has an inner diameter in a range of 0.5 mm to 3 mm. This embodiment is an eighth embodiment of the invention which is preferably dependent on the seventh embodiment of the invention.

A ninth embodiment of the invention is a system for providing a bone cement dough from two starting components, comprising an apparatus according to one of the preceding embodiments of the invention, wherein a tank containing a liquid component as the first starting component is stored in the receptacle, and comprising a plurality of syringes, in particular two, three, four or five syringes, each containing a powder component as the second starting component.

In one embodiment of the system, the apparatus comprises a plurality of ports, in particular two, three, four or five ports, wherein the number of ports corresponds to the number of syringes. This embodiment is a tenth embodiment of the invention which is preferably dependent on the ninth embodiment of the invention.

In one embodiment of the system, the syringes are reversibly fluidically connected to the ports. This embodiment is an eleventh embodiment of the invention which is preferably dependent on the tenth embodiment of the invention.

One embodiment of the system comprises an apparatus according to one of the sixth to eighth embodiments of the invention, in particular comprising compartments which have a substantially equal volume, wherein such an amount of liquid component is stored in the tank that, after the tank has been opened, all compartments of the reservoir can be filled with the liquid component and in this case have a fill level that projects at least in sections above a height of the at least one partition wall separating the compartments. This embodiment is a twelfth embodiment of the invention which is preferably dependent on the ninth to eleventh embodiments of the invention.

In one embodiment of the system, the fill level of the compartments projects at least in sections above the height of the partition wall by a maximum of 1 mm. This embodiment is a thirteenth embodiment of the invention which is preferably dependent on the twelfth embodiment of the invention.

In one embodiment of the system, a substantially equal amount of the powder component is stored in the syringes. This embodiment is a fourteenth embodiment of the invention which is preferably dependent on the ninth to thirteenth embodiments of the invention.

A fifteenth embodiment of the invention is a method for providing a bone cement dough from two starting components by means of a system according to one of the ninth to fourteenth embodiments of the invention, wherein the plurality of syringes comprises at least a first syringe and a second syringe, comprising the steps of:
- a. opening the tank by means of the opening means,
- b. flowing the liquid component from the opened tank into the reservoir,
- c. conveying a first part of the liquid component from the reservoir into the first syringe,
- d. conveying a second part of the liquid component from the reservoir into the second syringe.

In one embodiment of the method, wherein the system comprises a first port and a first conducting means for fluidically connecting the first port to the reservoir as well as a second port and a second conducting means for fluidically connecting the second port to the reservoir, the first part of the liquid component is conveyed from the reservoir into the first syringe via the first port and the second part of the liquid component is conveyed from the reservoir into the second syringe via the second port. This embodiment is a sixteenth embodiment of the invention which is preferably dependent on the fifteenth embodiment of the invention.

In one embodiment of the method, wherein the reservoir comprises a first compartment and a second compartment, wherein after the tank has been opened, the first part of the liquid component flows into the first compartment and the second part of the liquid component flows into the second compartment, wherein the first compartment is fluidically connected to the first port via the first conducting means and the second compartment is fluidically connected to the second port via the second conducting means, the first part of the liquid component is conveyed from the first compartment into the first syringe and the second part of the liquid component is conveyed from the second compartment into the second syringe. This embodiment is a seventeenth embodiment of the invention which is preferably dependent on the sixteenth embodiment of the invention.

General

In the present description, range specifications also include the values specified as limits. An indication of the type "in the range of X to Y" with respect to a variable A consequently means that A can assume the values X, Y and values between X and Y. Ranges delimited on one side of the type "up to Y" for a variable A correspondingly mean Y and less than Y as a value.

Some of the described features are linked to the term "substantially." The term "substantially" is to be understood as meaning that, under real conditions and manufacturing techniques, a mathematically exact interpretation of terms such as "superimposition," "perpendicular," "diameter," or "parallelism" can never be given exactly but only within certain manufacturing-related error tolerances. For example, "substantially parallel axes" include an angle of 85 degrees to 95 degrees to one another, and "substantially equal volumes" include a deviation of up to 5% by volume. An "apparatus consisting substantially of plastic material" comprises, for example, a plastics content of >95 to <100% by weight. A "substantially complete filling of a volume B" comprises, for example, a filling of >95 to <100% by volume of the total volume of B.

DETAILED DESCRIPTION

A first subject matter of the invention relates to an apparatus for providing a liquid component as a first starting component of a bone cement dough from two starting components, comprising a receptacle in which a tank containing the liquid component can be stored, an opening means for opening the tank, a reservoir, fluidically connected to the receptacle, for receiving the liquid component from the tank, at least one port for fluidically connecting the apparatus to a syringe in which a powder component can be stored as a second starting component of the bone cement dough, and at least one conducting means which fluidically connects the reservoir and the at least one port to one another.

The apparatus comprises a receptacle in which a tank containing the liquid component of the bone cement dough can be stored. A tank is understood to mean all vessels that can store the liquid component in a hermetically sealed and sterile manner and can be destroyed by manual application of force. Examples of tanks are glass ampules, plastic ampules, and plastic bags. Glass ampules are preferred because they are easy to sterilize and easy to open by manual application of force.

A receptacle is understood to mean a container, in particular a tubular container, of the apparatus that is suitable for securely storing the tank. The receptacle preferably comprises the tank, in particular the preferred glass ampule, in such a way that the tank is reliably secured against common jerky movements, for example when the apparatus is transported. For this purpose, a cushioning, for example made of a foam, can be attached within the receptacle, said cushioning reducing the risk of the tank opening in an undesired manner, for example as a result of breaking when the apparatus is transported.

In order to open the tank, the apparatus comprises an opening means. An opening means is understood to mean a means that is suitable for destroying the structural integrity of the tank and thus opening it. The embodiment of the opening means is to be selected on the basis of the type and structural stability of the tank. If the container is a plastic bag, for example, the opening means preferably comprises an element which is suitable for cutting, piercing or tearing open the plastic bag, for example a tip and/or a cutting edge. If the container is a glass ampule, for example, the opening means comprises or is, for example, a spike, a cutting edge or a breaking edge.

The container is preferably a glass ampule, and it is therefore preferred that the opening means comprises a bevel or consists of a bevel, the glass ampule being stored such that it can be pushed against said bevel in order to be opened. A glass ampule usually has a glass ampule head which is connected to a glass ampule body via a glass ampule neck. The glass ampule head can preferably be separated by being pushed against the bevel, so that the liquid component can flow from the tank out of the glass ampule neck opened thereby.

In one embodiment, the bevel is designed as a separate component arranged within the apparatus. In a further embodiment, the bevel is designed as a section of a wall, in particular of an inner wall, of the apparatus, in particular as a section of a wall of the receptacle or of a wall of the reservoir. This reduces the number of components of the apparatus and thus reduces the risk of malfunction of the apparatus and the production costs thereof.

In order to push the tank, in particular the glass ampule, against the bevel and thus open it, the apparatus, in particular the receptacle, can be designed in different ways. In one embodiment, the receptacle can be pushed at least in sections into the apparatus in order to push the tank against the bevel. For example, the receptacle can comprise a rear receiving section which can be inserted at least in sections into a front receiving section facing the opening means, in order to open the tank. In a further embodiment, the receptacle or at least a part of the receptacle can be bent in order to push the tank against the opening means, in particular in the form of the bevel, by means of a rotational movement against the opening means, in particular in the form of the bevel, and to open it in this way. In order to prevent unintentional opening of the tank, the apparatus can be designed with a transport securing device which prevents insertion of the receptacle or bending of the receptacle until the transport securing device is removed by a user of the apparatus before the apparatus is used.

In order to make it easier for the liquid component to flow from the tank, in particular a tank in the form of a glass ampule, after the opening thereof, the receptacle is preferably designed such that the tank assumes an angle to a perpendicular of the surface in a range of 10° to 30°, preferably 15° to 25°, when the apparatus is set up properly on a horizontal surface, for example a table.

The receptacle of the apparatus is fluidically connected to a reservoir. In this case, the receptacle and the reservoir can be designed to directly conduct fluid to one another, or a fluid-conducting element, for example a pipe or a tube, is arranged between the receptacle and the reservoir and produces a fluidic connection. The reservoir is used for the contamination-free, substantially sterile, intermediate storage of the liquid component, which flows from the tank after the opening thereof until it is mixed with a powder component as the second starting component of the bone cement dough. The reservoir stores the liquid component in a contamination-free manner and, when methymethacrylate is used as the liquid component, also substantially without odor nuisance for the user of the apparatus, in such a way that the liquid component can be removed easily, quickly, and in a volume according to need either as a whole or in a plurality of portion-wise removal operations in order to mix the bone cement dough. This allows time-offset mixing of a plurality of portions of bone cement dough. As a result, it is possible to always provide only a currently necessary amount of bone cement dough, to use it, and to only thereafter mix a further portion of bone cement dough from the same tank of the liquid component. Thus, the entire processing time of the bone cement dough used is available to the surgeon for each of these portions of the bone cement dough, which would not be possible if the entire tank were initially mixed.

In this case, the reservoir is preferably dimensioned such that the liquid component can be stored completely within the reservoir. For example, the reservoir holds a volume of up to 50 ml of a liquid.

In order to receive the liquid component, the reservoir can be designed in different ways. In one embodiment, the reservoir is designed in the manner of a shell in order to largely reduce the complexity of the apparatus. In this case, the reservoir preferably comprises a reservoir opening, which is fluidically open and faces the receptacle. This allows the liquid component to easily flow from the tank into the shell-like reservoir via the reservoir opening facing the receptacle.

When the apparatus is set up properly on a horizontal surface, the reservoir is preferably located spatially lower, i.e., closer to the horizontal surface, than the receptacle so that the liquid component can flow from the tank into the reservoir under the force of gravity and without intervention by a user.

In order to prevent the tank or tank fragments from entering the reservoir after the tank has been opened, in particular to prevent glass fragments from entering the reservoir after a tank in the form of a glass ampule has been opened, a retaining element can be arranged between the receptacle and the reservoir. The retaining element can, for example, comprise or consist of a sieve, an open-pore plate, in particular an open-pore plastic plate, or an open-pore pin, in particular an open-pore plastic pin.

In order to convey the liquid component from the reservoir into a syringe for further use, the apparatus comprises at least one port which is fluidically connected to the reservoir via a conducting means.

The conducting means can be formed differently in order to fluidically connect the port and the reservoir. For example, the conducting means can be formed as a channel. The conducting means is preferably connected to the reservoir in such a way that, when the apparatus is set up properly, substantially the entire liquid component present in the reservoir can be conveyed through the conducting means in the direction of the port. For example, the conducting means is arranged in the region of the point of the reservoir that is spatially lowest when the apparatus is set up properly.

Via the port, a syringe can be reversibly fluidically connected to the reservoir in order to convey the liquid component temporarily stored in the reservoir into the syringe. In order to produce the fluidic connection of the apparatus and the syringe, the port can be designed in different ways. In one embodiment, the port is formed as a thread in order to produce the fluidic connection with a corresponding counterpart on the syringe. For example, the port can comprise an internal thread which forms the fluidic connection with an external thread on a syringe. In a further embodiment, the port and the syringe form a bayonet connection. In a further embodiment, the port and the syringe can be fluidically connected to one another by partial insertion of the syringe into the port. For example, the conducting means can be formed as a tube in order to fluidically connect the reservoir and the port, and a syringe can form the fluidic connection of the port and the syringe at the port via section-wise insertion of the syringe into the tube. After conveying the liquid component, the syringe can be detached from the port for further use.

In order to prevent tank fragments, in particular glass fragments resulting from a tank in the form of a glass ampule being opened, from entering a syringe that is fluidically connected to the port, the port can be equipped with a filter unit. The filter unit can, for example, comprise or consist of a sieve, an open-pore plate, in particular an open-pore plastic plate, or an open-pore pin, in particular an open-pore plastic pin. In one embodiment, the port and the filter unit are irreversibly connected to one another, for example via an adhesive connection. In a further embodiment, the port and the filter unit are reversibly connected to one another; the filter unit is, for example, formed as an adapter that can be connected to the port. In this case, the adapter can, for example, be connected to the port via a threaded connection or a bayonet connection. With a side facing away from the port, the adapter can, for example, in turn be fluidically connected to the syringe so that the port is fluidically connected to the syringe via the adapter.

In order to prevent an accidental flow of the liquid component via the at least one port into a syringe fluidically connected to the at least one port, it is preferred that when the apparatus is set up properly on a horizontal surface, the reservoir is located spatially lower, i.e., closer to the horizontal surface, than the at least one port.

One embodiment of the apparatus is characterized in that the apparatus comprises a plurality of ports, in particular two, three, four or five ports, for fluidically connecting the apparatus to a syringe in which a powder component can be stored as the second starting component of the bone cement dough, and a plurality of conducting means, in particular two, three, four or five conducting means, wherein one of the conducting means of the plurality of conducting means in each case fluidically connects the reservoir and one of the ports of the plurality of ports to one another. The apparatus comprises a plurality of conducting means/port pairs in order to be able to fluidically connect the apparatus to a plurality of syringes at the same time. As a result of the plurality of ports, the apparatus can already be fluidically connected to a plurality of syringes before the first mixing of a portion of bone cement dough, which makes it easier for a user of the apparatus to use a plurality of syringes in the course of the surgery. Moreover, in the event of an obstruction of one of the ports, it is possible to resort to another port.

One embodiment of the apparatus is characterized in that the reservoir is divided into a plurality of compartments, wherein one of the compartments is in each case fluidically connected to one of the ports via one of the conducting means. As a result of the compartments, the reservoir is divided into smaller sub-reservoirs, which allows the liquid component flowed from the tank to be pre-portioned within the reservoir. Since the individual compartments are each fluidically connected to a separate port via a separate conducting means, a pre-portioned liquid component amount can be removed from the apparatus via each of these separate ports. This ensures that only one desired, predefined amount of liquid component can ever be removed from one of the ports, which makes use easier for the user of the apparatus.

In one embodiment, the individual compartments have different volumes so that different amounts of the liquid component can be removed from the corresponding ports of the apparatus. This allows different portions of bone cement dough from a tank containing the liquid component to be mixed in a temporally staggered manner. The portions can, for example, differ in volume and/or viscosity.

One embodiment of the apparatus is characterized in that the individual compartments each have a substantially equal volume. This allows the temporally staggered mixing of substantially equal portions of bone cement dough by means of a single tank of the liquid component. The portions can, for example, be equal in their volumes and viscosities, while simultaneously using an equal part of powder component.

In order to provide pre-portioned amounts of the liquid component via the individual ports, the reservoir can be divided into the compartments in different ways.

One embodiment of the apparatus is characterized in that the reservoir is divided into the compartments by means of at least one partition wall. For example, a single partition wall can divide the reservoir into two compartments, or two intersecting partition walls can divide the reservoir into four compartments. Partition walls allow simple and cost-effective construction of the reservoir divided into compartments.

One embodiment of the apparatus is characterized in that the compartments are in each case fluidically open at an upper compartment side facing the receptacle, so that the compartments are fluidically connected to one another via the upper compartment sides. For example, a first partition wall can divide the reservoir, in particular a shell-like reservoir, which comprises a reservoir side that is fluidically open and faces the receptacle, into two compartments which each comprise an upper compartment side that is fluidically open and faces the receptacle. Furthermore, the reservoir can be divided, for example, by a second partition wall which crosses the first partition wall, into four compartments with correspondingly four upper compartment sides which are fluidically open.

The conducting means can be formed differently in order to fluidically connect the reservoir or the individual compartments of the reservoir to the port or the ports.

One embodiment of the apparatus is characterized in that the at least one conducting means is a tube. A tube allows for a simple, favorable, and flexible fluidic connection of reservoir and port.

One embodiment of the apparatus is characterized in that the tube has an inner diameter in a range of 0.5 mm to 3 mm, preferably between 0.5 mm and 2.5 mm, more preferably between 0.5 mm and 2 mm. Due to the surface tension of the liquid component, such an inner diameter of the tube prevents the liquid component from autonomously flowing from the reservoir through the conducting means in the direction of the port. With such an inner diameter of the tube, the liquid component remains within the reservoir until the user actively causes said liquid component to be conveyed from the reservoir in the direction of the port, for example by exerting a delivery pressure on the liquid component or by applying a negative pressure through the conducting means from the direction of the port, for example exerted by actuating a syringe fluidically connected to the port.

A further subject matter of the invention relates to a system for providing a bone cement dough from two starting components, comprising an apparatus according to one of the preceding embodiments, wherein a tank, preferably a tank in the form of a glass ampule, containing a liquid component as the first starting component is stored in the receptacle, and wherein the system comprises a plurality of syringes, in particular two, three, four or five syringes, wherein the syringes each contain a powder component as the second starting component.

A tank is understood to mean all vessels that can store the liquid component in a hermetically sealed and sterile manner and can be destroyed by manual application of force. Examples of tanks are glass ampules, plastic ampules, and plastic bags. Glass ampules are preferred because they are easy to sterilize and easy to open by manual application of force.

The system comprises a plurality of syringes which contain a powder component as the second starting component of the bone cement dough. After the liquid component has been conveyed from the tank via the reservoir, the conducting means and the port into one of the syringes, this allows the bone cement dough to be easily and rapidly mixed directly in said syringe. There is thus no need to transfer the bone cement dough into one of the syringes. In order to mix the bone cement dough in the syringe, the latter can contain a mixing device, such as a mixing rod or one or more mixing balls. A mixing ball is used to mix the bone cement dough by shaking the syringe, in that the mixing ball, together with the two starting components, is moved back and forth in the syringe by the shaking and thereby supports the mixing.

In one embodiment of the system, the syringes are designed without a mixing device.

A syringe is to be understood as a container which can store the powder component in a contamination-free manner and by means of which a bone cement dough can be applied to a desired location. The syringe preferably comprises a syringe piston which can discharge the bone cement dough from the syringe by advancing in the direction of a discharge opening of the syringe. In order to discharge the bone cement dough, a discharge aid, such as a cannula, a discharge spout or a tube, can be fastened to the syringe, in particular to the discharge opening.

The syringe can be reversibly fluidically connected to the port of the apparatus. For this purpose, the syringe can comprise, for example, a thread, in particular an external thread, or a part of a bayonet connection.

In order to prevent fragments of the tank from transferring with the liquid component into the syringe, the syringe may comprise a filter. The filter can, for example, comprise or consist of a sieve, an open-pore plate, in particular an open-pore plastic plate, or an open-pore pin, in particular an open-pore plastic pin. In one embodiment, the syringe and the filter are reversibly connected to one another; the filter is, for example, formed as a syringe adapter that can be connected to the syringe. In this case, the syringe adapter can, for example, be connected to the syringe via a threaded connection or a bayonet connection. Before the bone cement dough is applied from the syringe, the filter is preferably removed from the syringe, for example by unscrewing. In a further embodiment, the filter is inserted into the syringe in the region of the discharge opening and is pushed out of the syringe, in particular out of the discharge opening, by the bone cement dough when the bone cement dough is discharged.

The system is preferably designed such that the liquid component contained is sufficient for mixing an applicable bone cement dough that can be used for surgeries, in a plurality of, preferably all, syringes of the system. For example, the tank contains 30 ml of liquid component and the plurality of syringes contains a total of 45 g of powder component.

The system allows time-offset mixing of a plurality of portions of bone cement dough from a single package, in particular by means of a single tank of the liquid component. This reduces the time pressure on a surgeon, who otherwise would have to use the entire initially mixed bone cement dough within the processing time thereof. The time-offset, portion-wise mixing starts a separate processing time for each of the syringes so that overall a longer period of time is available for the use of the bone cement dough.

In order to prevent an accidental flow of the liquid component via the at least one port into a syringe fluidically connected to the at least one port, it is preferred that when the apparatus is set up properly on a horizontal surface, the reservoir is located spatially lower, i.e., closer to the horizontal surface, than the at least one port. It is moreover preferred that, when the apparatus is arranged properly on a horizontal surface, the liquid component, after flowing into the reservoir, has a liquid level that is spatially lower than the at least one port.

One embodiment of the system is characterized in that the apparatus comprises a plurality of ports, in particular two, three, four or five ports. It is preferred that the system comprises as many syringes as ports. For example, the system comprises two ports and two syringes.

This allows all syringes to be simultaneously fluidically connected to the apparatus even before the beginning of a surgery, which makes the surgical procedure easier for the surgeon.

One embodiment of the system is characterized in that the syringes are reversibly fluidically connected to the ports. This closes both the apparatus and the syringes in a contamination-free manner so that the system, in particular the tank and the powder component within the system, can be stored in a sterile manner. In particular, such a system can be removed from a sterile packet without this representing a risk of contamination for the system, in particular the tank and the powder component within the system. Moreover, possible application errors of the system by a surgeon are reduced as a result.

One embodiment of the system, wherein the apparatus of the system is an apparatus according to one of the preceding embodiments of the apparatus, which comprises a reservoir which is divided into a plurality of compartments by means of at least one partition wall, and wherein the compartments are each fluidically open at an upper compartment side facing the receptacle, so that the compartments are fluidically connected to one another via the upper compartment sides, and wherein one of the compartments is in each case fluidically connected via one of the conducting means to one of the ports of the apparatus, is characterized in that such an amount of liquid component is stored in the tank that, after the tank has been opened, all compartments of the reservoir can be filled with the liquid component and in each case have a fill level that projects at least in sections above a height of the at least one partition wall separating the respective compartments.

This allows all compartments to be filled with the liquid component since the liquid component flowing from the tank into the reservoir is distributed via the upper compartment sides over the particular separating partition wall.

For example, the liquid component flows from the tank only into one of the compartments of the reservoir and fills it. If the volume of this compartment is filled, further liquid component flowing into this compartment flows from the already filled compartment over the partition wall of the compartment into an adjacent compartment. In this way, the monomer liquid can be distributed successively into all compartments of the reservoir and fill them. In this case, the amount of liquid component is adapted such that it is possible to completely fill all compartments and that, in each of the compartments, the liquid component has a fill level that is higher, at least in sections, than the corresponding partition wall. This allows the fill level of the monomer liquid to be "equalized" over all compartments. The compartments thus have an excess which projects above the at least one partition wall.

One embodiment of the system is characterized in that the fill level of the compartments projects at least in sections above the height of the at least one partition wall by no more than 1 mm. In other words, the excess is not higher than 1 mm. This allows good distribution of the liquid component into all compartments. With the discharging of the first compartment, the excess flows into the first compartment and is discharged as well. This ensures, for example, that, despite equally sized compartments, the compartment first discharged supplies the largest proportion of liquid component. The small excess of a maximum of 1 mm ensures that the compartments provide substantially the volume of liquid component predefined by the compartments irrespective of the sequence of their discharging.

One embodiment of the system is characterized in that a substantially equal amount of the powder component is stored in the syringes. This prevents the risk of confusion of the individual syringes, which would in some circumstances deliver bone cements with different properties, such as their rheology. Moreover, the compartments preferably have substantially equal volumes so that a bone cement dough having substantially the same properties, in particular substantially the same rheology, is obtainable with each syringe.

A further subject matter of the invention relates to a method for providing a bone cement dough from two starting components by means of a system, in particular by means of a system according to one of the preceding embodiments, wherein the plurality of syringes comprises at least a first syringe and a second syringe, comprising the steps of:

a. opening the tank by means of the opening means, b. flowing the liquid component from the opened tank into the reservoir, c. conveying a first part of the liquid component from the reservoir into the first syringe, d. conveying a second part of the liquid component from the reservoir into the second syringe.

The tank can be opened in different ways, wherein it is preferred that the tank is a glass ampule and the glass ampule is opened by pushing or rotationally moving the glass ampule against the opening means, preferably against the opening means in the form of a bevel. In this case, a glass ampule head is preferably separated off, which opens the tank.

After the tank has been opened, the liquid component flows from the opened tank into the reservoir, preferably the shell-like reservoir. Preferably, this takes place under the force of gravity and without active intervention by a user of the system.

In order to be able to provide a first portion of the bone cement dough, the first part of the liquid component is conveyed from the reservoir into the first syringe. The second part of the liquid component remains in the reservoir.

The second part of the liquid component is conveyed into the second syringe at a time offset from the conveying of the first part of the liquid component. A further part of the liquid component can still remain in the reservoir and be available for conveying into a further syringe and for additional conveying into the first or second syringe.

The conveying of the liquid component into the first syringe and the second syringe can be carried out in different ways. In a preferred embodiment of the method, the conveying takes place in each case by a piston stroke of a syringe piston associated with the syringes. As a result, conveying can be carried out without separate tools or equipment, such as a pump, which makes the method easier.

One embodiment of the method, wherein the system comprises a first port and a first conducting means for fluidically connecting the first port to the reservoir as well as a second port and a second conducting means for fluidically connecting the second port to the reservoir, is characterized in that the first part of the liquid component is conveyed from the reservoir into the first syringe via the first port and the second part of the liquid component is conveyed from the reservoir into the second syringe via the second port. Further parts of the liquid component can be conveyed into further or the same syringes via further ports which are fluidically connected to the reservoir via further conducting means.

In this way, the first syringe and the second syringe can be simultaneously fluidically connected to the apparatus, for example even before the beginning of a surgery, which makes the application of the method easier. Moreover, the system can already be packaged in a sterile manner with fluid-conducting syringes, which reduces the risk of contamination of the system after unpacking from the sterile packaging.

One embodiment of the method, wherein the reservoir comprises a first compartment and a second compartment, is characterized in that, after the tank has been opened, the first part of the liquid component flows into the first compartment and the second part of the liquid component flows into the second compartment, wherein the first compartment is fluidically connected to the first port via the first conducting means and the second compartment is fluidically connected to the second port via the second conducting means, and the first part of the liquid component is conveyed from the first compartment into the first syringe and the second part of the liquid component is conveyed from the second compartment into the second syringe.

By means of the first compartment and the second compartment, and optionally further compartments, the liquid component is pre-portioned in the reservoir so that only a substantially predefined amount of liquid component can be removed from the apparatus via the ports. A user of the system therefore does not have to pay attention to how much of the liquid component is conveyed into the particular syringe, which reduces the risk of incorrectly metered removal of the liquid component.

Bone cement dough is understood to mean a substance that is suitable in the field of medical technology for creating a stable connection between artificial joints, such as hip and knee joints, and bone material and/or for stabilizing verte-bral bodies. By curing, a bone cement dough becomes a bone cement. These bone cements are preferably polymethyl methacrylate bone cements (PMMA bone cements) or inorganic bone cements.

PMMA bone cements have been used for a long time in medical applications and are based on the work of Sir Charnley (cf. Charnley, J. Anchorage of the femoral head prosthesis of the shaft of the femur. *J. Bone Joint Surg.* 1960; 42, 28-30.). In this case, PMMA bone cements can be produced from a powder component comprising a bone cement powder as the first starting component and a liquid component comprising a monomer liquid as the second starting component. With a suitable composition, the two starting components can be storage-stable separately from one another. When the two starting components are brought into contact with one another, a plastically deformable bone cement dough is produced by the swelling of the polymer components of the bone cement powder. In this case, polymerization of the monomer by radicals is initiated. As the polymerization of the monomer progresses, the viscosity of the bone cement dough increases until it cures completely.

Bone cement powder is understood to mean a powder that comprises at least one particulate polymethyl methacrylate and/or a particulate polymethyl methacrylate copolymer. Examples of copolymers are styrene and/or methyl acrylate. In one embodiment, the bone cement powder can additionally comprise a hydrophilic additive which supports the distribution of the monomer liquid within the bone cement powder. In a further embodiment, the bone cement powder can additionally comprise an initiator which initiates the polymerization. In a further embodiment, the bone cement powder can additionally comprise a radiopaque material. In yet another embodiment, the bone cement powder can additionally comprise pharmaceutically active substances, such as antibiotics.

The bone cement powder preferably comprises, as a hydrophilic additive, at least one particulate polymethyl methacrylate and/or a particulate polymethyl methacrylate copolymer, an initiator, and a radiopaque material, or consists of these components. More preferably, the bone cement powder comprises at least one particulate polymethyl methacrylate and/or a particulate polymethyl methacrylate copolymer, an initiator, a radiopaque material, and a hydrophilic additive, or consists of these components. Most preferably, the bone cement powder comprises at least one particulate polymethyl methacrylate and/or a particulate polymethyl methacrylate copolymer, an initiator, a radiopaque material, a hydrophilic additive, and an antibiotic, or consists of these components.

According to the invention, the particle size of the particulate polymethyl methacrylate and/or of the particulate polymethyl methacrylate copolymer of the bone cement powder can correspond to the sieve fraction of less than 150 μm, preferably less than 100 μm.

According to the invention, the hydrophilic additive can be designed in particulate and/or fibrous form. In a further embodiment, the hydrophilic additive can be slightly soluble, preferably insoluble, in methyl methacrylate. In a further embodiment, the hydrophilic additive can have an absorption capacity of at least 0.6 g of methyl methacrylate per gram of hydrophilic additive. In a further embodiment, the hydrophilic additive can comprise a chemical substance comprising at least one OH group. In this case, the hydrophilic additive can preferably have covalently bonded OH groups at its surface. Examples of such preferred hydrophilic additives can be additives selected from the group comprising cellulose, oxycellulose, starch, titanium dioxide and silicon dioxide, wherein pyrogenic silicon dioxide is particularly preferred. In one embodiment, the particle size of the hydrophilic additive can correspond to the sieve fraction of less than 100 μm, preferably less than 50 μm, and most preferably less than 10 μm. The hydrophilic additive can be contained in an amount of 0.1 to 2.5% by weight, based on the total weight of the bone cement powder.

According to the invention, the initiator can contain dibenzoyl peroxide or consist of dibenzoyl peroxide.

According to the invention, a radiopaque material is understood to mean a substance that makes it possible to make the bone cement visible on diagnostic X-ray images. Examples of radiopaque materials can include barium sulfate, zirconium dioxide, and calcium carbonate.

According to the invention, the pharmaceutically active substance can comprise one or more antibiotics and optionally added cofactors for the one or more antibiotics. Preferably, the pharmaceutically active substance consists of one or more antibiotics and optionally added cofactors for the one or more antibiotics. Examples of antibiotics include, inter alia, gentamicin, clindamycin, and vancomycin.

According to the invention, the monomer liquid can comprise the monomer methyl methacrylate or consist of methyl methacrylate. In one embodiment, the monomer liquid comprises, in addition to the monomer, an activator dissolved therein, such as N,N-dimethyl-p-toluidine, or consists of methyl methacrylate and N,N-dimethyl-p-toluidine.

An inorganic bone cement is understood to mean a bone cement based on calcium phosphates and calcium sulfate dihydrate. Powders of calcium phosphates and/or calcium sulfate dihydrate that can be cured by a liquid component comprising an aqueous solution of different salts are used as powder components in this case. A large number of inorganic bone cements have been described, of which the following are mentioned by way of example: EP 1 592 463 B1, EP 2 271 585 B1, and EP 2 988 789 B1.

The features disclosed for the apparatus are also disclosed for the system and the method, and vice versa.

FIGURES

In the following, the invention is illustrated further, by way of example, by figures. The invention is not limited to the figures. The figures show:

FIG. 1 a schematic longitudinal section of an apparatus for providing a liquid component as a first starting component of a bone cement dough from two starting components, containing a tank comprising the liquid component, FIG. 2 a schematic longitudinal section of a system for providing a bone cement dough, comprising the apparatus of FIG. 1, the tank of FIG. 1, a first syringe and a second syringe, FIG. 3 the system of FIG. 2 with an open tank, FIG. 4 the system of FIGS. 2 and 3 when a part of the liquid component is conveyed into the first syringe, FIG. 5 the system of FIGS. 2 to 4 with a fluidically separated first syringe, FIG. 6 the system of FIGS. 2 to 5 with a fluidically separated second syringe, FIG. 7 a schematic longitudinal section of a further system for providing a bone cement dough from two starting components, FIG. 8 a schematic longitudinal section of a further system for providing a bone cement dough from two starting components, comprising a reservoir divided into compartments and a tank containing a liquid component,

FIG. 9 a schematic plan view of a detail of the system of FIG. 8, comprising the reservoir, FIG. 10a schematic side view of the reservoir of FIGS. 8 and 9, FIG. 11 the system of FIGS. 8 to 10 with an open tank, FIG. 12 the system of FIGS. 8 to 11 after conveying a part of the liquid component into a first syringe, and FIG. 13a flow chart of a method for providing a bone cement dough.

Figure 1:
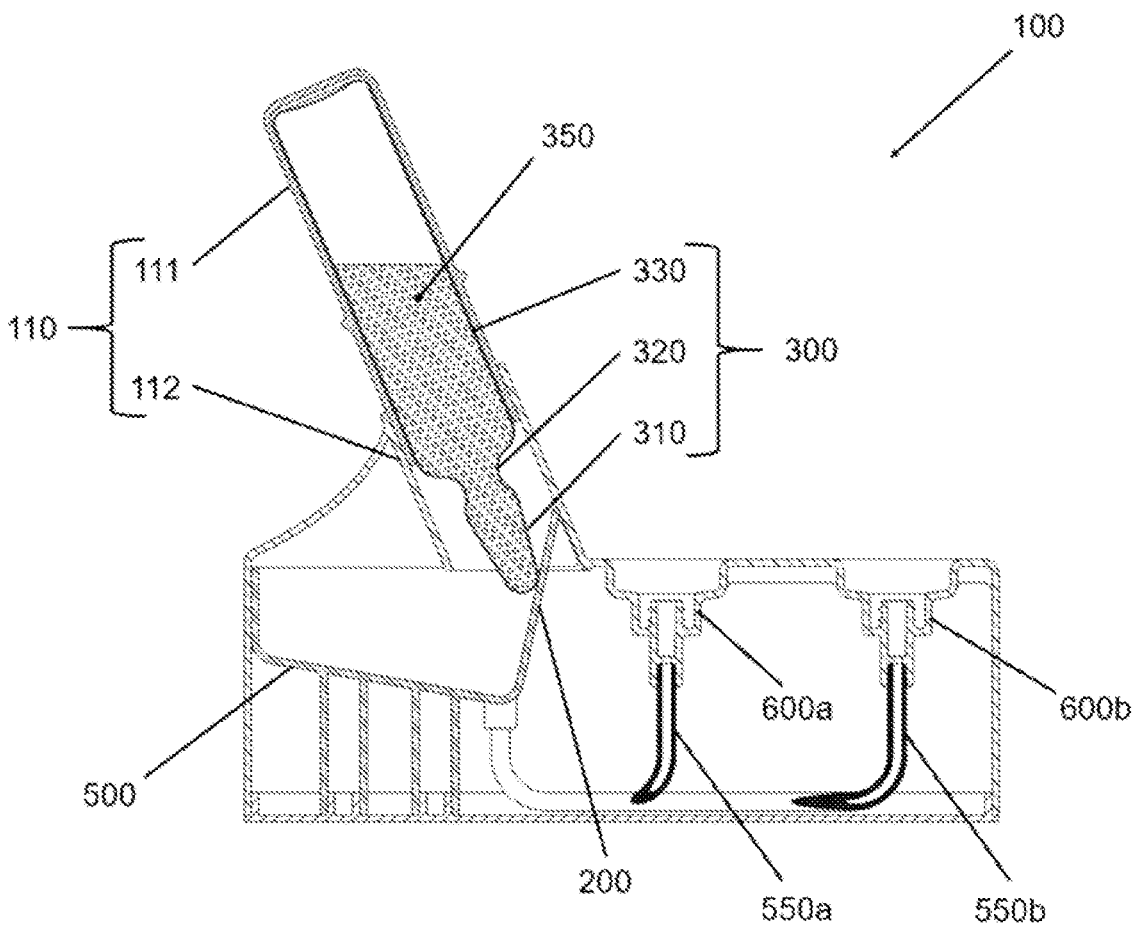
FIG. 1 shows a schematic longitudinal section of an exemplary embodiment of an apparatus 100 for providing a liquid component as a first starting component of a bone cement dough from two starting components. The apparatus 100 comprises a tubular receptacle 110 in which a tank 300 containing a liquid component 350 as the first starting component of the bone cement dough is stored. The tank 300 is a glass ampule comprising a glass ampule head 310 which is connected to a glass ampule body 330 via a glass ampule neck 320. The receptacle 110 comprises the tank 300 in the manner of a sleeve, so that it can be securely transported in the apparatus 100. The receptacle 110 is directly fluidically connected to a reservoir 500 formed in the manner of a shell. In order to open the tank 300, the receptacle 110 comprises a rear receiving section 111 which can be inserted into a front receiving section 112 so that the tank 300, in particular the glass ampule body 330, is stored such that it can be pushed against an opening means 200 in the form of a bevel. In the embodiment shown, the opening means 200 is designed as part of a wall of the reservoir 500.

The apparatus 100 comprises a first port 600a and a second port 600b, via which the apparatus 100 can be reversibly fluidically connected to syringes, in particular to two syringes simultaneously, in particular by screwing together. The the first port 600a is fluidically connected to the reservoir 500 via a first conducting means 550a and the second port 600b is fluidically connected to the reservoir via a second conducting means 550b. The two conducting means 550a, 550b are designed in the form of two separate tubes, both of which form a separate access to the reservoir.

Figure 2:
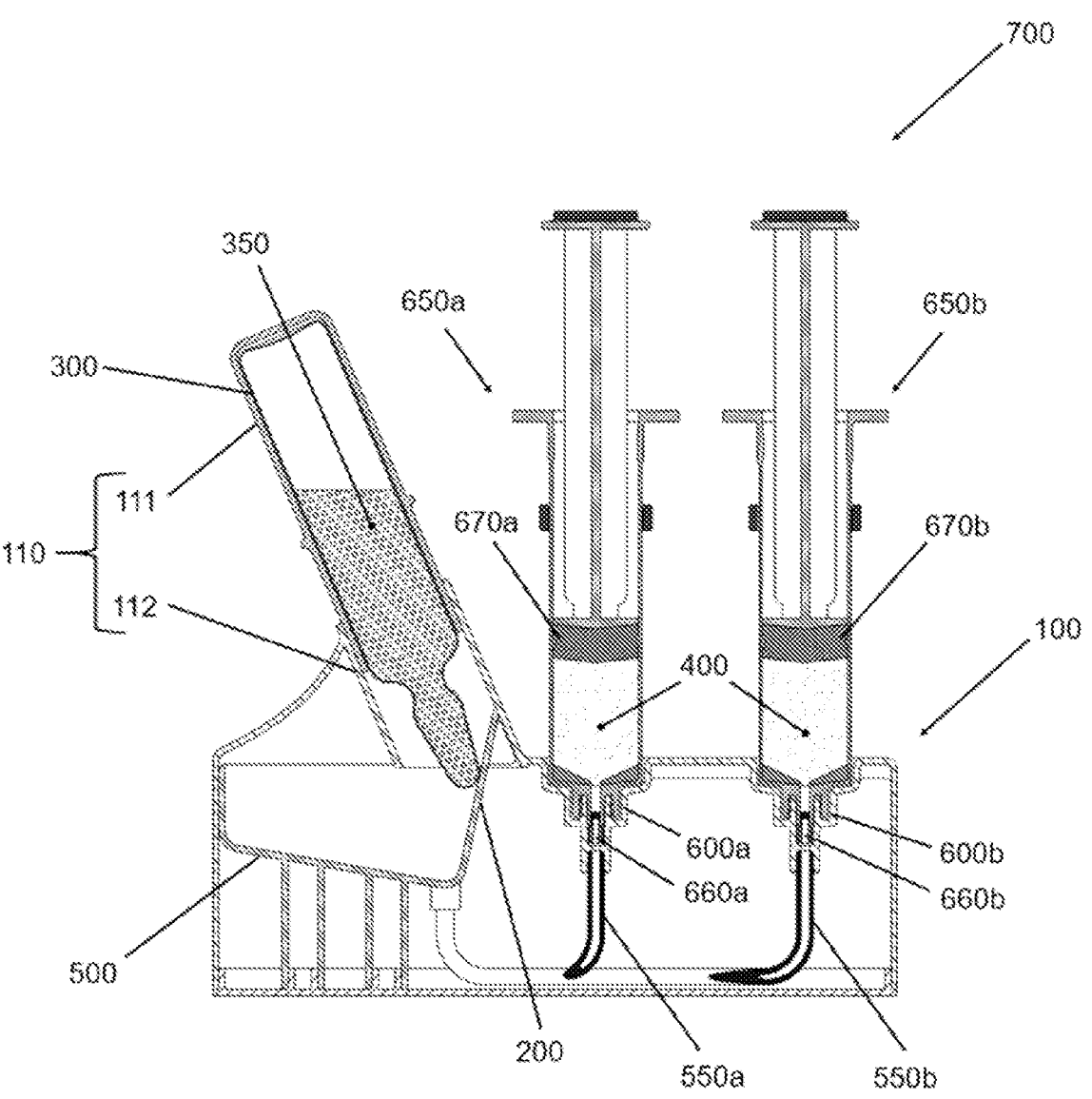

FIG. 2 shows a system 700 for providing a bone cement dough from two starting components, comprising the apparatus 100 of FIG. 1, the tank 300 of FIG. 1 filled with the liquid component 350 as the first starting component of the bone cement dough, as well as a first syringe 650a and a second syringe 650b. The syringes 650a, 650b contain a powder component 400 as the second starting component of the bone cement dough and are each equipped with a syringe piston 670a, 670b which is stored so as to be reversibly displaceable along a longitudinal axis of the syringes 650a, 650b. The syringes 650a, 650b are furthermore each equipped with a fluid-conducting filter 660a, 660b so that fluids, in particular gases and the liquid component 350, but no solids, in particular the powder component 400 and/or parts of the tank 300, can be exchanged between the syringes 650a, 650b and the apparatus 100 via the conducting means 550a, 550b. The first syringe 650a is reversibly fluidically connected to the apparatus 100 via the first port 600a and the second syringe 650b is reversibly fluidically connected to the apparatus via the second port 600b, wherein the syringes 650a, 650b are connected to the ports 600a, 600b via threads.

Figure 3:
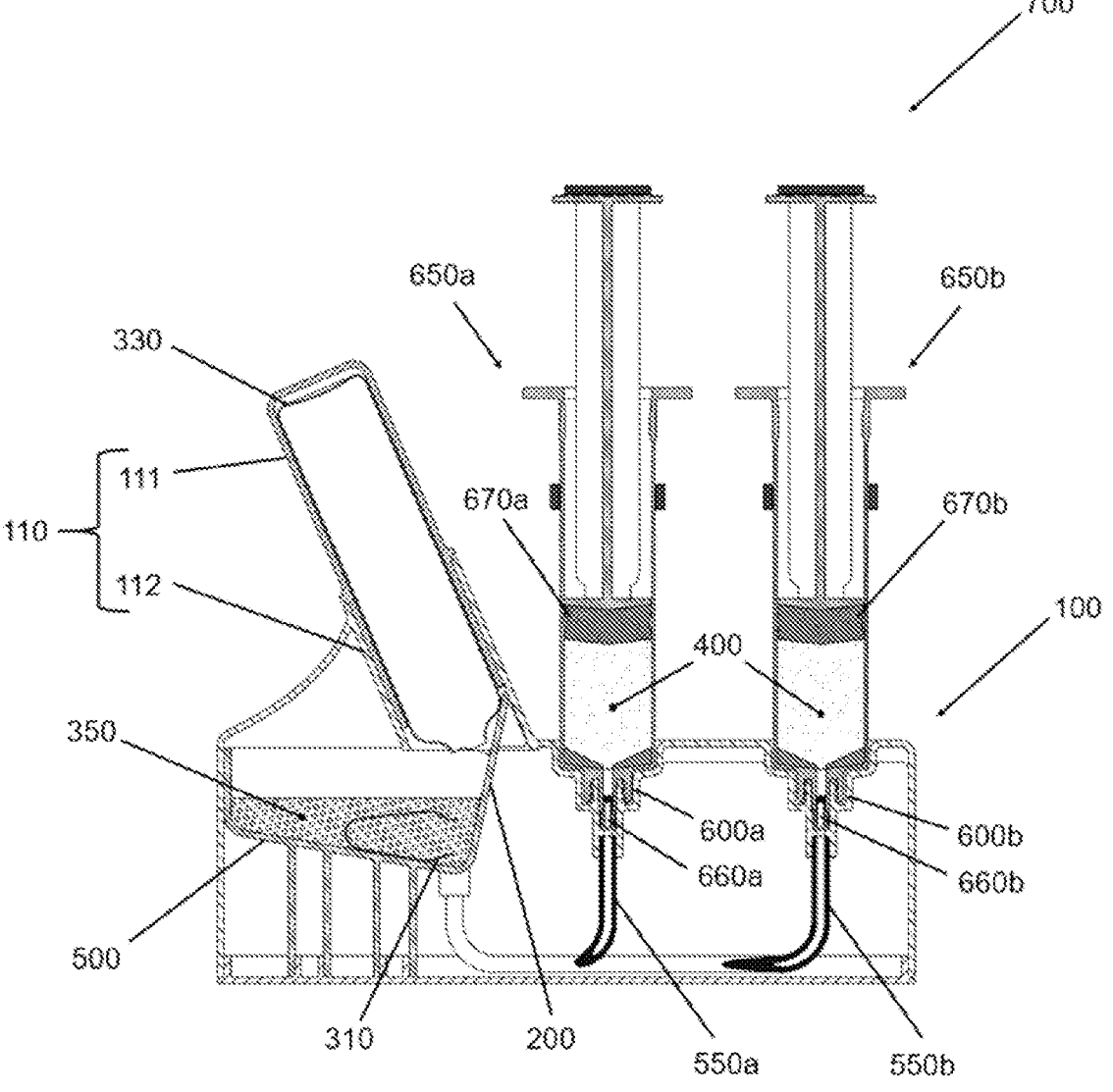

FIG. 3 shows the system 700 of FIG. 2, wherein, in comparison to FIG. 2, the rear receiving section 111 is inserted in sections into the front receiving section 112. By inserting the rear receiving section 111 into the front receiving section 112, the tank head 310 has been pushed against the opening means 200 and thereby broken off, as a result of which the liquid component 350 has flowed into the reservoir 500. In order to facilitate the liquid component 350 flowing out of the tank 300, the latter is arranged in the receptacle 110 at an angle of approximately 20° to a perpendicular of the apparatus 100. Due to the surface tension of the liquid component 350, the liquid component 350 remains in the reservoir 500 and does not flow autonomously in the direction of the syringes 650a, 650b through the conducting means 550a, 550b. The liquid component 350 is thus temporarily stored in the reservoir 500 in a contamination-free manner and can be conveyed as needed and in a time-independent and time-offset manner into the syringes 650a, 650b.

Figure 4:
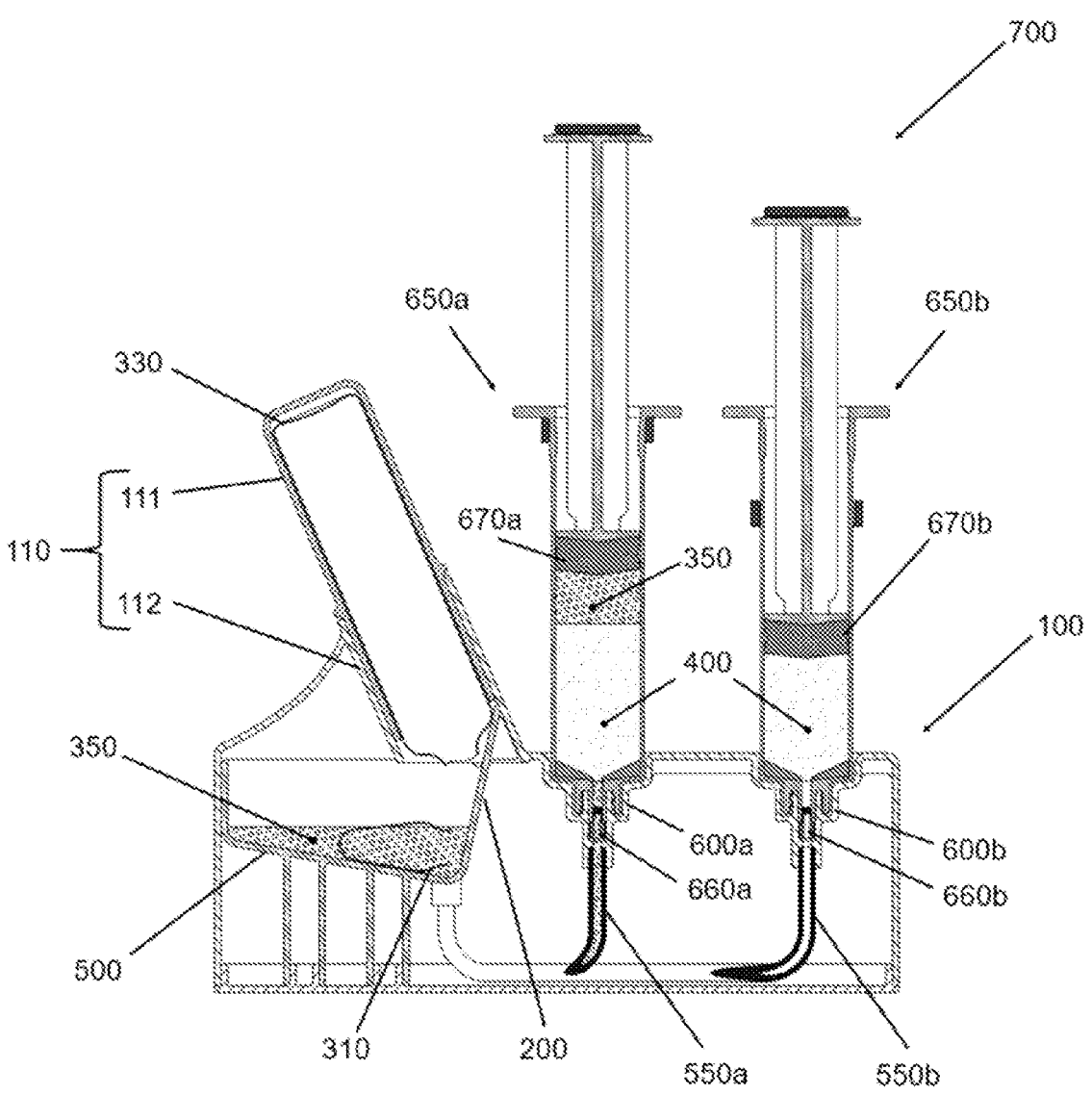

FIG. 4 shows the system 700 of FIGS. 2 and 3, wherein, in comparison to FIG. 2, a part of the liquid component 350 has been conveyed from the reservoir 500 via the first conducting means 550a into the first syringe 650a. In order to convey the liquid component 350, the syringe piston 670a of the first syringe 650a was partially pulled out of an end, axially opposite the first port 600a, of the first syringe 650a, whereby a negative pressure in the first syringe 650a caused the part of the liquid component 350 to be conveyed from the reservoir 500. The further the syringe piston 670a of the first syringe 650a is pulled out, the more liquid component 350 is conveyed into the first syringe 650a. In order to determine the delivered amount of liquid component 350, a user of the system can, for example, read a scale on an outer side of the first syringe 650a (not shown). In a further embodiment, which is not shown, the system 700 comprises a piston stroke regulator on the syringes 650a, 650b so that, in order to convey the liquid component 350 from the reservoir 500, the syringe pistons 670a, 670b can be pulled out of the syringes 650a, 650b only up to a predefined height. The piston stroke regulator allows a predetermined amount of the liquid component 350 to be conveyed into the syringes 650a, 650b without the user of the system 700 having to read a scale. The piston stroke regulator can be adapted to the amount of powder component 400 in the syringes 650a, 650b so that a bone cement dough that has a desired rheology can be provided in the syringes 650a, 650b.

Figure 5:
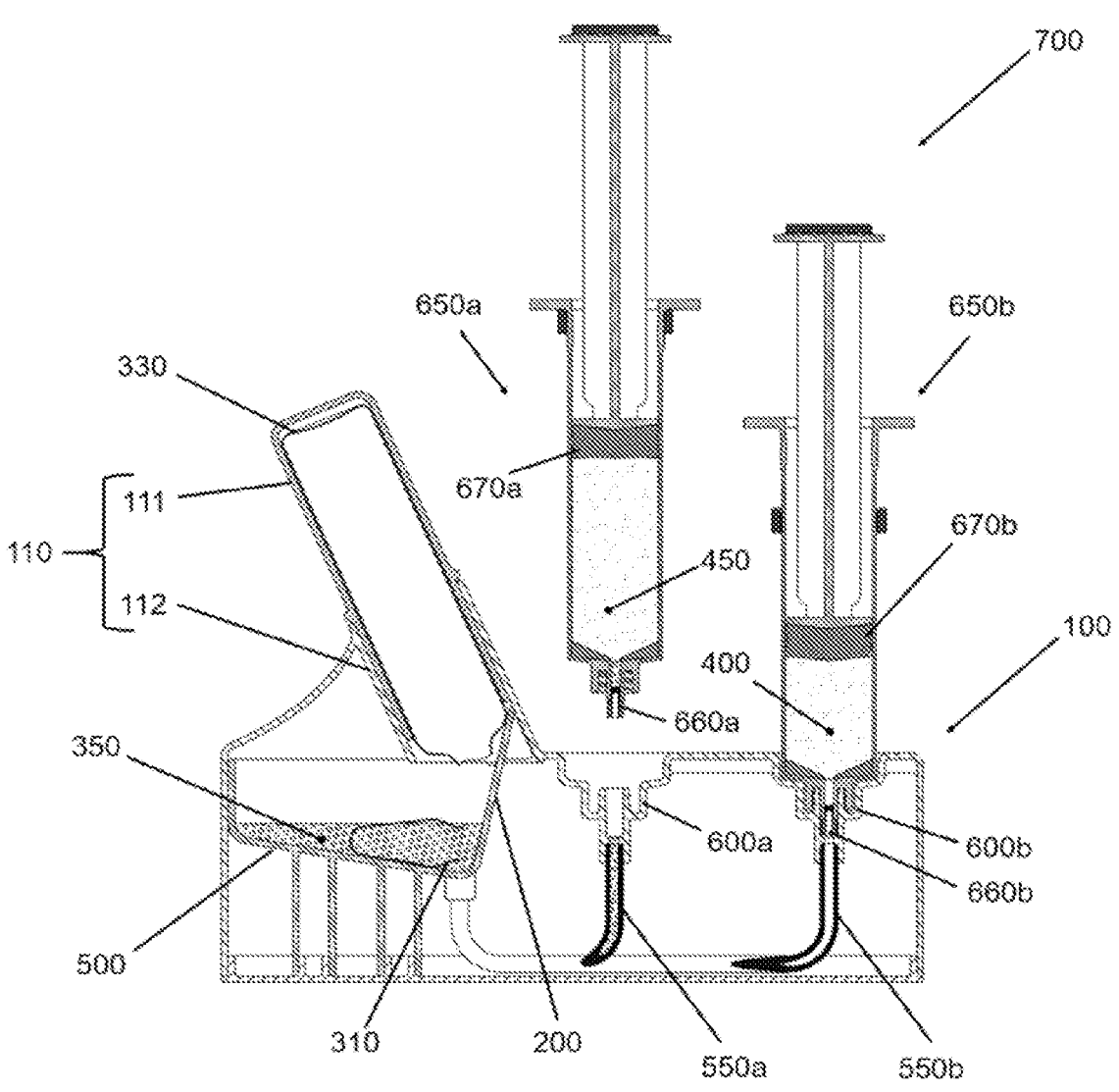

FIG. 5 shows the system 700 of FIGS. 2 to 4, wherein, in comparison to FIG. 4, the first syringe 650a has been fluidically separated from the apparatus 100. In the first syringe 650a, a bone cement dough 450 has been formed from the two starting components in the first syringe 650a by shaking the first syringe 650a, which bone cement dough can be used within its processing period. Also located within the first conducting means 550a are residues of the liquid component 350, which residues were not conveyed into the first syringe 650a. Located in the reservoir 500 is a remaining part of the liquid component 350, which part is available at any time for conveying through the second conducting means 550b into the second syringe 650b. Conveying the liquid component 350 into the second syringe 670b may take place in the same way as conveying into the first syringe 650a.

Figure 6:
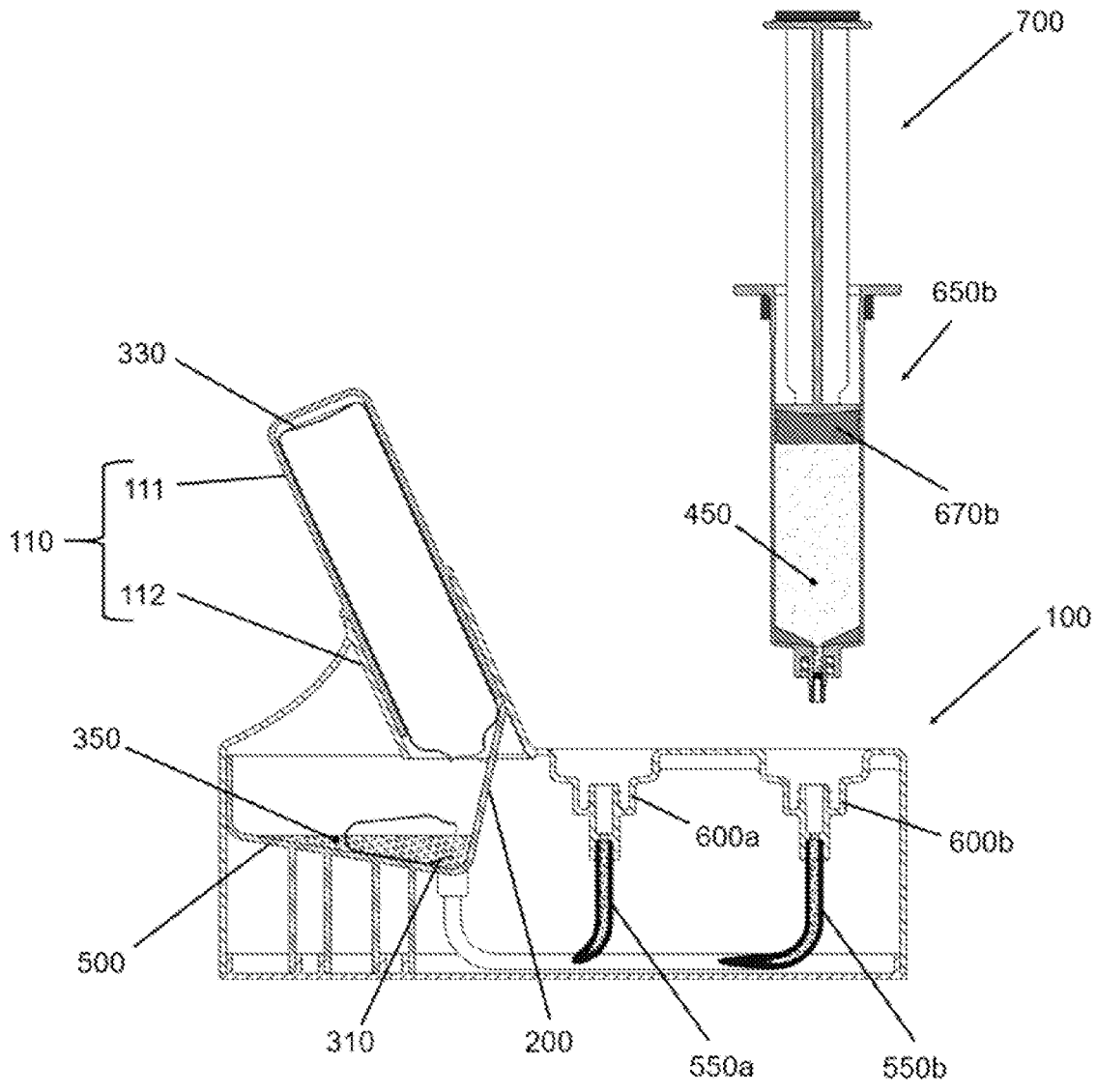

FIG. 6 shows the system 700 of FIGS. 2 to 5, wherein the first syringe 650a is no longer shown. In FIG. 6, in comparison to FIG. 5, a further part of the liquid component 350 was conveyed from the reservoir 500 via the second conducting means 550b and the second port 600b into the second syringe 650b, the second syringe 650b was then fluidically separated from the second port 600b, and the two starting components in the second syringe 650b were mixed by shaking the second syringe 650b to form the bone cement dough 450. The bone cement dough 450 provided in the second syringe 650b can be used in a processing period which is independent of the processing period of the bone cement dough 450 provided in the first syringe 650a (cf. FIG. 5). The processing periods of the bone cement doughs 450 in the two syringes 650a, 650b of the system 700 are not started at the same time. The system 700 thus makes it possible to provide second portions of the bone cement dough 450, which portions can be used temporally independently of one another. In further embodiments, which are not shown, the system 700 may comprise more than two ports 600a, 600b and more than two syringes 650a, 650b in order to provide more than two portions of bone cement dough 450.

Figure 7:
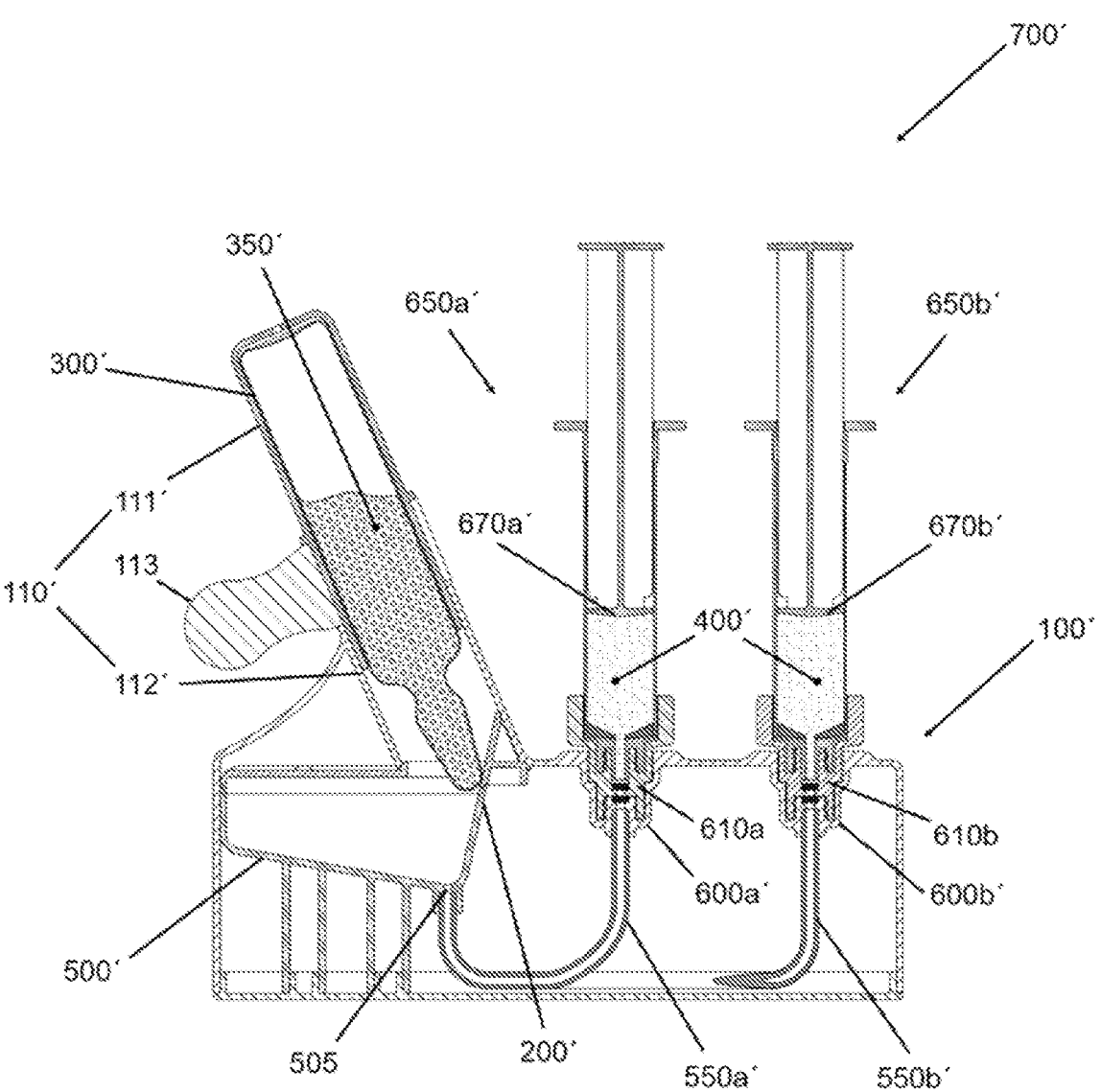

FIG. 7 is a schematic longitudinal section of a further exemplary embodiment of a system 700' for providing a bone cement dough from two starting components, comprising an apparatus 100', a tank 300' containing a liquid component 350' as the first starting component, as well as a first syringe 650a' and a second syringe 650b' containing a powder component 400' as the second starting component. The embodiment of the system 700' largely corresponds to the embodiment described above and shown in FIGS. 2 to 6, and therefore reference is made to the above description in order to avoid repetitions. Modifications to an embodiment shown in FIGS. 2 to 6 have the same reference sign with an additional apostrophe.

On the receptacle 110', in particular on the rear receiving section 111', the apparatus 100' comprises a transport securing device which prevents insertion of the rear receiving section 111' into the front receiving section 112'. This ensures that the tank 300' is not opened unintentionally, for example during the transport of the system 770'. The transport securing device 113 surrounds the receptacle 110' in the manner of a sleeve and can be removed therefrom by simply pulling it, in order to enable insertion of the rear receiving section 111' into the front receiving section 112'.

The two syringes 650a', 650b' of the system 700' comprise no filters 660a, 660b, in contrast to the two syringes 650a, 650b of the system 700 of FIGS. 2 to 6. Instead, the apparatus 100' is equipped with a fluid-conducting filter unit 610a, 610b in the form of an adapter that can be attached to the two ports 600a', 600b'. The filter units 610a, 610b are arranged between the syringes 650a', 650b' and the ports 600a', 600b' so that gases and the liquid component 350' can be conveyed from the reservoir 500' into the syringes 650a', 650b', but solids, such as the powder component 400' or parts of the tank 300', cannot pass through. The use of the system 700' for providing the bone cement dough, in particular second portions of the bone cement dough, largely corresponds to the use of the system 700 of FIGS. 2 to 6.

FIG. 7 shows, in contrast to the preceding figures, a reservoir duct 505 fluidically connecting the reservoir 500 and the first conducting means 550a'. Such a reservoir duct 505 also connects the second conducting means 550b' of the system 700' as well as the two conducting means 550a, 550b of the apparatus 100 of FIGS. 1 to 6 (not shown in each case).

Figure 8:
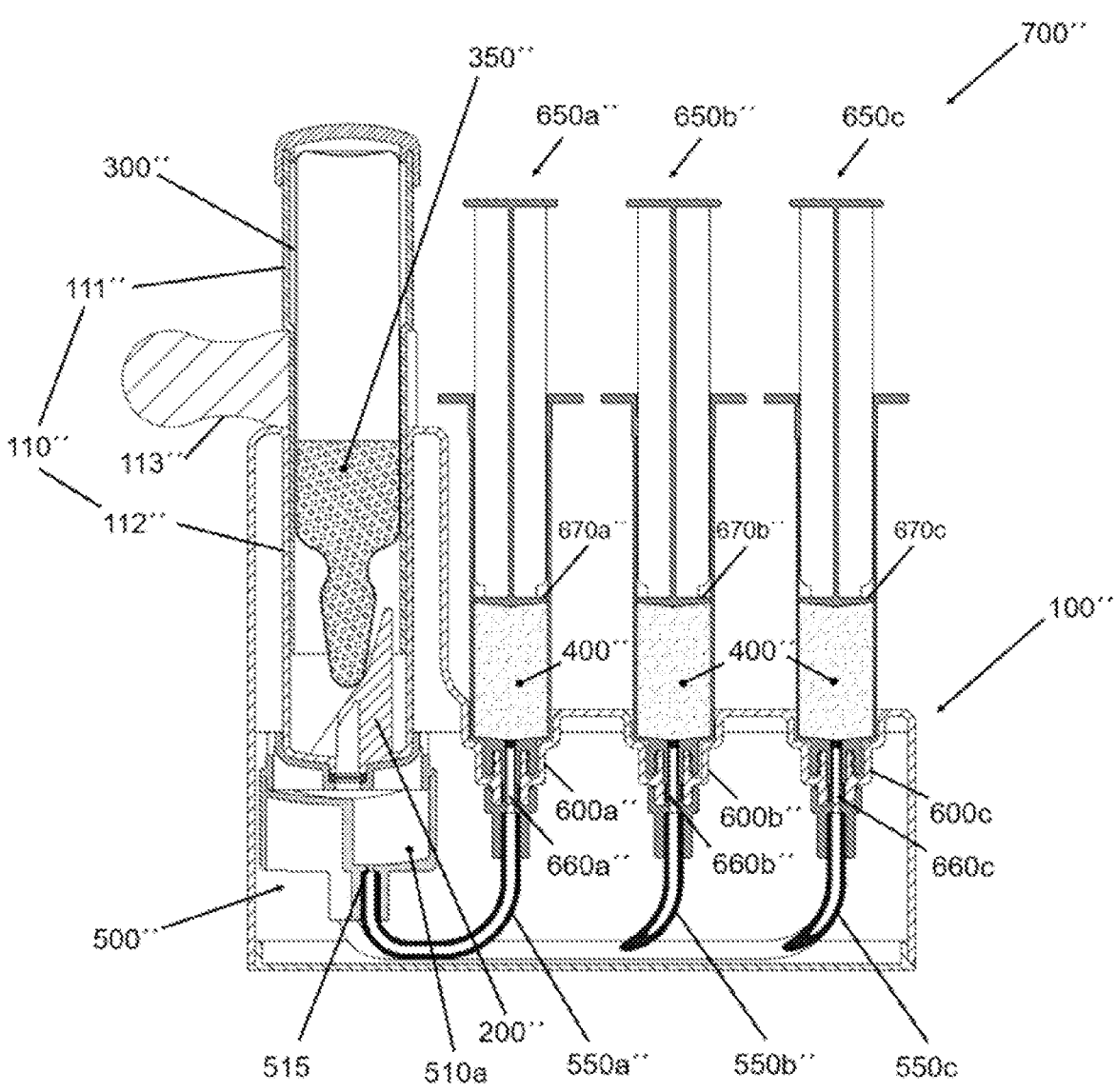

FIG. 8 shows a schematic longitudinal section of a further exemplary embodiment of a system 700" for providing a bone cement dough from two starting components. The embodiment of the system 700" largely corresponds to the embodiments described above and shown in FIGS. 2 to 6 and in FIG. 7, and reference is therefore made to the above description in order to avoid repetitions. Modifications to an embodiment shown in FIGS. 2 to 6 or FIG. 7 have the same reference sign with two apostrophes.

In comparison to the embodiments described above, the system 700" comprises, in addition to the first port 660a" and the second port 600b", a third port 600c which is fluidically connected to the reservoir 500" via a third conducting means 550c. The third conducting means 550c is designed to be separate from the other two conducting means 550a", 550b". The third port 600c is reversibly fluidically connected to a third syringe 650c, wherein, like the two other syringes 650a", 650b", the third syringe 650c contains the powder component 400" and is equipped with a fluid-conducting filter 660c in order to prevent solids, in particular the powder component 400" and/or parts of the tank 300", from passing between the third syringe 650c and the apparatus 100". The third syringe 650c comprises a syringe piston 670c which can be axially displaced in the third syringe 650c.

Between the tank 300" and the reservoir 500", the opening means 200" in the form of a bevel is arranged in the receptacle 110", in particular in the front receiving section 112", wherein, in contrast to the preceding embodiments, said opening means is not designed as part of the reservoir 500".

The reservoir 500" is divided into three compartments 510a, 510b, 510c, wherein only a first compartment 510a of the three compartments 510a, 510b, 510c is visible in FIG. 8. Each of the compartments 510a, 510b, 510c is fluidically connected to one of the ports 600a", 600b", 600c. The first compartment 510a is fluidically connected to the first port 600a" via the first conducting means 550a", the second compartment 510b (not shown in FIG. 8; see, for example, FIG. 9 or 10) is fluidically connected to the second port 600b" via the second conducting means 550b", and the third compartment 510c (not shown in FIG. 8; see, for example, FIG. 9 or 10) is fluidically connected to the third port 600c via the third conducting means 550c. For this purpose, each compartment 510a, 510b, 510c comprises a compartment duct 515 which opens into the relevant conducting means 550a", 550b", 550c and thus produces a fluidic connection (only the compartment duct 515 of the first compartment 510a is visible).

Figure 9:
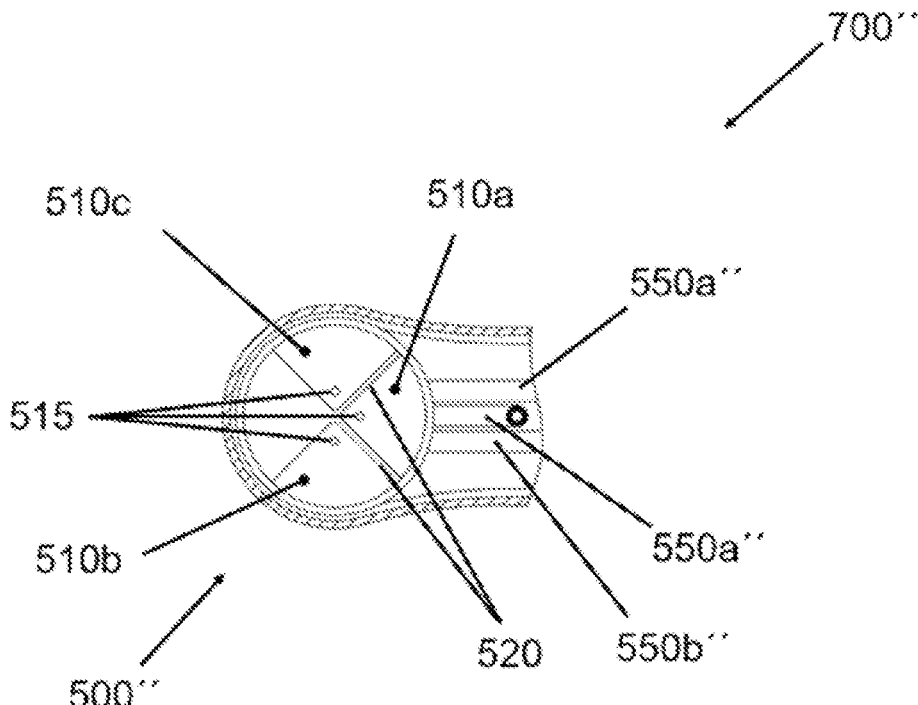

FIG. 9 is a detail of the system 700" of FIG. 8 comprising the reservoir 500", in a plan view of a longitudinal axis of the system 700". The first compartment 510a is separated from the second compartment 510b and from the third compartment 510c by a partition wall 520 in each case. The individual compartments 510a, 510b, 510c are in each case fluidically connected to the respective conducting means 550a", 550b", 550c" by one of the compartment ducts 515.

Figure 10:
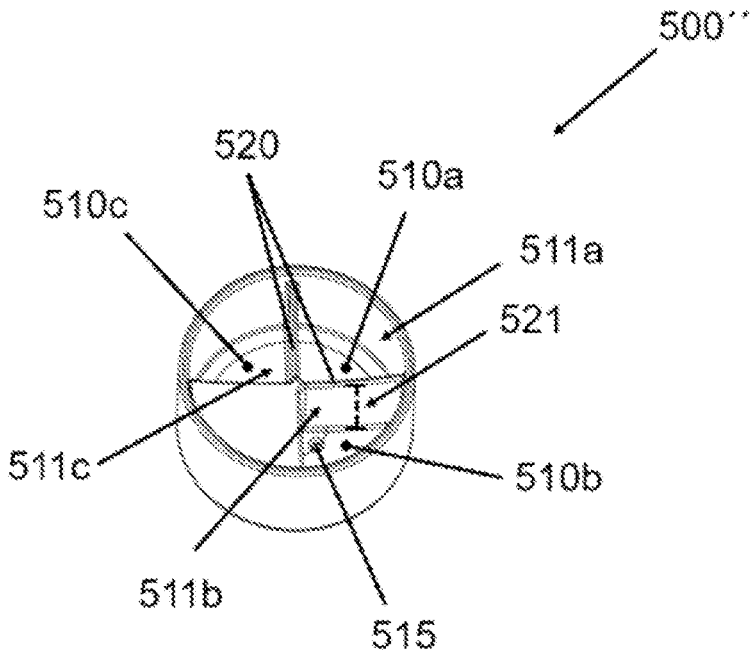

FIG. 10 shows a perspective side view of the reservoir 500" of the system 700" of FIGS. 8 and 9, which reservoir is divided into compartments 510a, 510b, 510c. The two partition walls 520 separating the compartments 510a, 510b, 510c each have a height 521 (only marked for the partition wall 521 separating the first compartment 510a and the second compartment 510b) which co-determines the volumes of the individual compartments 510a, 510b, 510c. The volumes of the individual compartments 510a, 510b, 510c are substantially equal so that the same amount of liquid component 350" (not marked) can be stored in each compartment 510a, 510b, 510c. In the shown embodiment of the reservoir 500", the height 521 of the partition walls 520 is not constant over the entire extension of the respective partition walls 520. In further embodiments, which are not shown, the height 521 of the partition walls 520 is constant over the entire extension. The compartments 510a, 510b,

510c each comprise a fluidically open, upper compartment side 511a, 511b, 511c which faces the receptacle 110" of FIG. 8 and through which the liquid component 350" can flow after the tank 300" of FIG. 8 has been opened.

Figure 11:
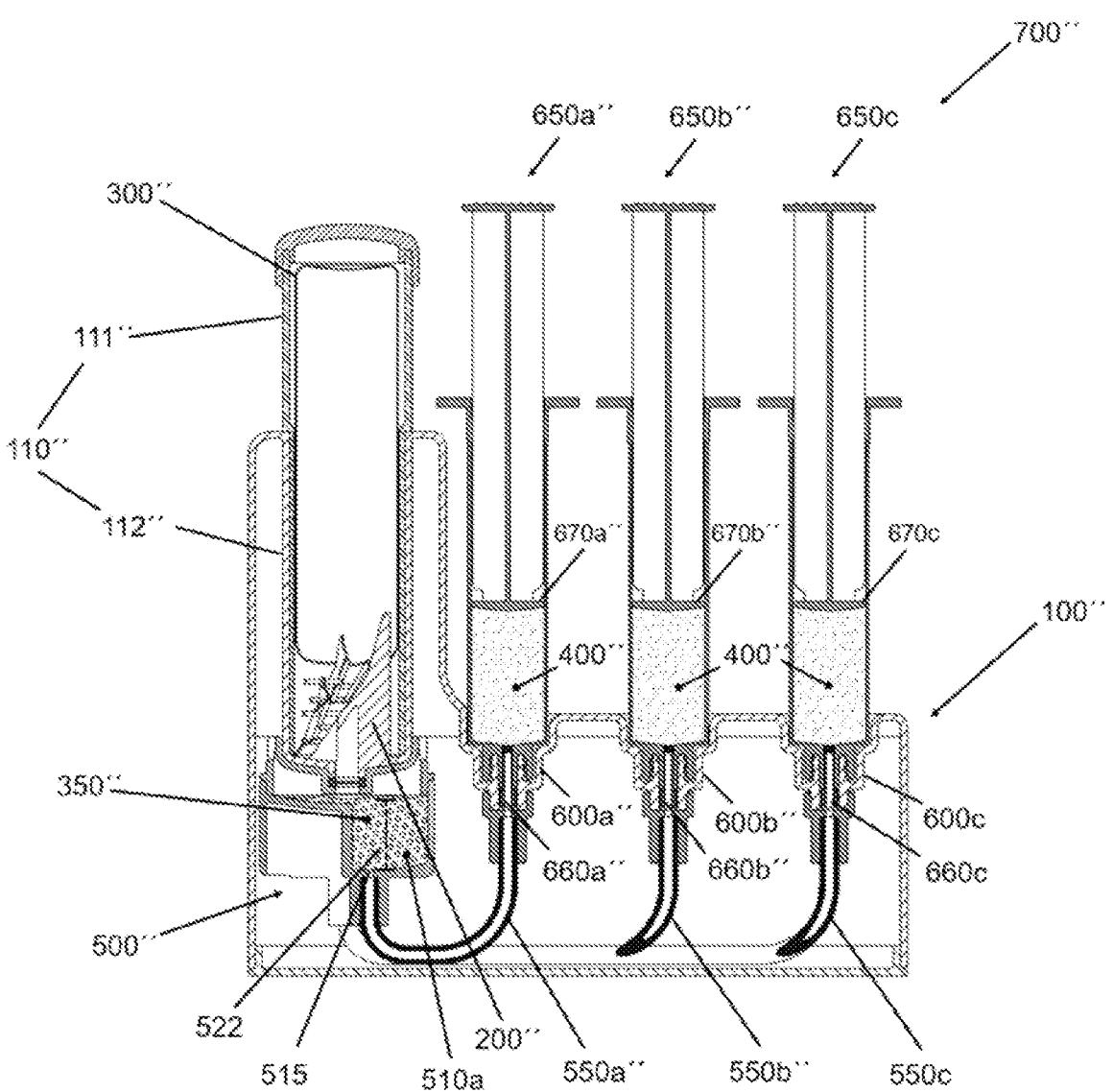

FIG. 11 shows the system 700" of FIGS. 8 to 10, wherein, in comparison to FIG. 8, the rear receiving section 111' has been inserted in sections into the front receiving section 112' after removal of the transport securing device 113" of FIG. 8, whereby the tank 300" has been pushed against the opening means 200" and has thus been fluidically opened. The liquid component 350" has flowed from the tank 300" into the reservoir 500", in particular through the upper compartment sides 511a, 511b, 511c of FIG. 10, and has filled the compartments 510a, 510b, 510c (only shown for the first compartment 510a). The amount of liquid component 350" is selected such that the compartments 510a, 510b, 510c in this case have a fill level 522 which projects at least in sections above the height 521 (cf. FIG. 10) of the partition walls 520. As a result, the compartments 510a, 510b, 510c have an excess of liquid component 350" which extends above the upper compartment sides 511a, 511b, 511c. The excess has allowed all compartments 510a, 510b, 510c to be filled evenly, so that it was irrelevant whether the liquid component 350" from the tank 300" flowed evenly into all compartments 510a, 510b, 510c or unevenly only into the first compartment 510a, for example. The excess of liquid component has ensured adaptation of the fill level of the individual compartments 510a, 510b, 510c since the compartments 510a, 510b, 510c are fluidically connected to one another via the upper compartment sides 511a, 511b, 511c.

The fill level 522 of the compartments 510a, 510b, 510c is only 1 mm higher than the height of the partition walls 520 so that substantially an equal amount of liquid component 350" can be conveyed in each of the syringes 650a", 650b", 650c.

Figure 12:
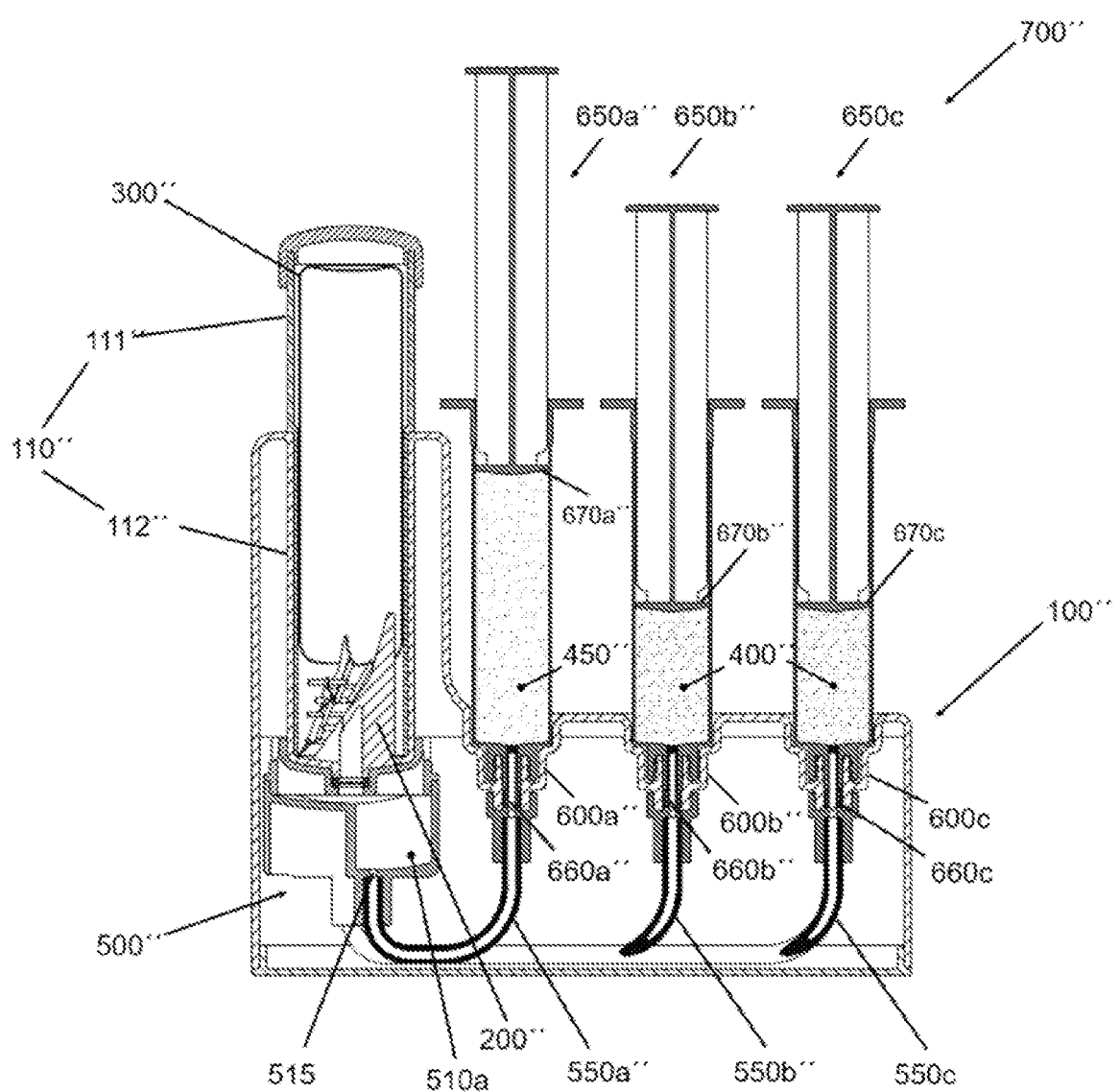

FIG. 12 shows the system 700" of FIGS. 8 to 11, wherein, in comparison to FIG. 11, the liquid component 350" (not visible) was conveyed from the first compartment 510a via the first conducting means 550a" and the first port 600a" into the first syringe 650a" by partially axially pulling the syringe piston 670a" out of the first syringe 650a". A bone cement dough 450" from the two starting components has thereby formed in the first syringe 650". In the second compartment 510b and in the third compartment 510c, there is still liquid component 350" at a fill level 522 which corresponds to the lowest height 521 of the partition walls 520 (not shown). In comparison to the provision in the first syringe 650a", this allows for time-offset provision of the bone cement dough 450" in the second syringe 650b" and the third syringe 650c with the aforementioned advantages.

Figure 13:
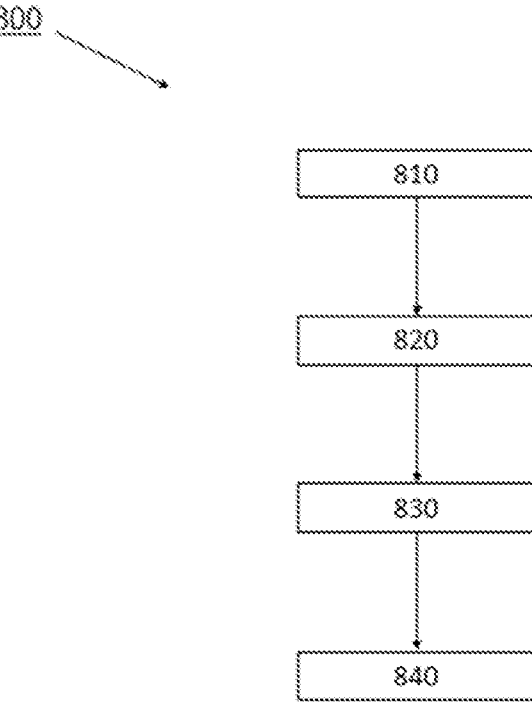

FIG. 13 is a flow chart of a method 800 for providing a bone cement dough 350, 350', 350" by means of the systems 700, 700', 700" according to FIGS. 2 to 6, 7, and 8 to 12, comprising steps 810 to 840.

In a step 810, the tank 300, 300', 300" stored in the receptacle 110, 110', 110" is opened by means of the opening means 200, 200', 200". The tank 300, 300', 300" is preferably opened 810 by inserting the rear receiving section 11, 111', 111" into the front receiving section 112, 112', 112", whereby the tank 300, 300', 300", preferably in the form of a glass ampule, is pushed against the opening means 200, 200', 200", preferably in the form of a bevel, and thereby opened.

In a step 820, after the tank 300, 300', 300" has been opened, the liquid component 350, 350', 350" flows out of said tank and into the reservoir 500, 500', 500". In one embodiment of the method 800, the liquid component 350" flows into a reservoir 500" divided into separate compartments 510a, 510b, 510c, which allows pre-portioning of the liquid component 350" within the reservoir 500" and makes portion-wise and time-offset mixing of the bone cement dough 450" easier for a user of the method 800.

In a step 830, a first part of the liquid component 350, 350', 350" is conveyed from the reservoir into the first syringe 650a, 650a', 650a".

In one embodiment, conveying 830 takes place from the first compartment 510a into the first syringe 650a, 650a', 650a".

After this step 830, a first portion of the bone cement dough 450, 450', 450" can be provided in the first syringe 650a, 650a', 650a" by mixing the two starting components. Preferably, the first syringe 650a, 650a', 650a" is designed without a mixing device and the provision can be carried out without mechanical action but by shaking the first syringe 650a, 650a', 650a", for example. After providing the bone cement dough 450, 450', 450" in the first syringe 650a, 650a', 650a", the processing time of the bone cement dough 450, 450', 450" begins. The bone cement dough 450, 450', 450" is preferably used within this processing time.

After a time offset, for example after the expiry of the processing time of the bone cement dough 450, 450', 450" in the first syringe 650a, 650a', 650a" or after the consumption of the bone cement dough 450, 450', 450" in the first syringe 650a, 650a', 650a", and independently of step 830, a second part of the liquid component 350, 350', 350" is conveyed from the reservoir into the second syringe 650b, 650b', 650b" in a step 840.

In one embodiment, conveying 840 takes place from the second compartment 510b into the second syringe 650a, 650a', 650a".

After this step 840, a second portion of the bone cement dough 450, 450', 450" can be provided in the second syringe 650b, 650b', 650b" by mixing the two starting components. Preferably, the second syringe 650b, 650b', 650b" is designed without a mixing device and the provision can be carried out without mechanical action but by shaking the second syringe 650b, 650b', 650b", for example. After providing the bone cement dough 450, 450', 450" in the second syringe 650b, 650b', 650b", the processing time of the bone cement dough 450, 450', 450" begins. The bone cement dough 450, 450', 450" is preferably used within this processing time.

The method 800 allows the bone cement dough 450, 450', 450" to be provided in portions, which represents a simplification for a user of the method. In particular, the time pressure for carrying out the method 800 is reduced for the user due to the specific processing time of the bone cement dough 450, 450', 450" used. This allows a broader selection of different compositions of the bone cement dough 450, 450', 450". Moreover, the method enables a more resource-efficient use of a single tank 300, 300', 300" of the liquid component 350, 350', 350".

REFERENCE SIGNS

100, 100', 100" Apparatus
110, 110', 110" Receptacle
111, 111', 111" Rear receiving section
112, 112', 112" Front receiving section
113, 113" Transport securing device
200, 200', 200" Opening means
300, 300', 300" Tank
310 Glass ampule head

320 Glass ampule neck
330 Glass ampule body
350, 350', 350" Liquid component
400, 400', 400" Powder component
450, 450', 450" Bone cement dough
500, 500', 500" Reservoir
505 Reservoir duct
510a First compartment
510b Second compartment
510c Third compartment
511a, 511b, 511c Upper compartment side
515 Compartment duct
520 Partition wall
521 Height of the partition wall
522 Fill level
550a, 550a', 550a" First conducting means
550b, 550b', 550b" Second conducting means
550c Third conducting means
600a, 600a', 600a" First port
600b, 600b', 600b" Second port
600c Third port
610a, 610b Filter unit
650a, 650a', 650a" First syringe
650b, 650b', 650b" Second syringe
650c Third syringe
660a, 660b Filter
660a", 660b", 660c
670a, 670b, Syringe piston
670a', 670b'
670a", 670b", 670c
700, 700', 700" System
800 Method for providing a bone cement dough
810 Opening
820 Flowing
830 First conveying
840 Second conveying

The invention claimed is:

1. An apparatus for providing a liquid component as a first starting component of a bone cement dough from two starting components, comprising a receptacle in which a tank containing the liquid component can be stored, an opening means for opening the tank, a reservoir, fluidically connected to the receptacle, for receiving the liquid component from the tank, at least one port for fluidically connecting the apparatus to a syringe in which a powder component can be stored as a second starting component of the bone cement dough, and at least one conducting means fluidically connecting the reservoir and the at least one port to one another;

wherein the at least one port comprises a plurality of ports for fluidically connecting the apparatus to a syringe in which a powder component can be stored as the second starting component of the bone cement dough, and the at least one conducting means comprises a plurality of conducting means, wherein one of the conducting means of the plurality of conducting means in each case fluidically connects the reservoir and one of the ports of the plurality of ports to one another;

wherein the reservoir is divided into a plurality of compartments, and wherein one of the compartments is in each case fluidically connected to one of the ports via one of the conducting means; and wherein the reservoir is divided into the compartments by means of at least one partition wall.

2. The apparatus according to claim 1, wherein the compartments each have a substantially equal volume.

3. The apparatus according to claim 1, wherein the compartments are in each case fluidically open at an upper compartment side facing the receptacle, so that the compartments are fluidically connected to one another via the upper compartment sides.

4. The apparatus according to claim 1, wherein the at least one conducting means is a tube.

5. The apparatus according to claim 4, wherein the tube has an inner diameter in a range of 0.5 mm to 3 mm.

6. A system for providing a bone cement dough from two starting components, comprising an apparatus according to claim 1, wherein a tank containing a liquid component as the first starting component is stored in the receptacle, and comprising a plurality of syringes, each containing a powder component as the second starting component.

7. The system according to claim 6, wherein the number of ports of the plurality of ports corresponds to the number of syringes.

8. The system according to claim 7, wherein the syringes are reversibly fluidically connected to the ports.

9. The system according to claim 6, wherein a substantially equal amount of the powder component is stored in the syringes.

10. A method for providing a bone cement dough from two starting components by means of a system according to claim 6, wherein the plurality of syringes comprises at least a first syringe and a second syringe, comprising the steps of:

1. Opening the tank by means of the opening means,
2. flowing the liquid component from the opened tank into the reservoir,
3. conveying a first part of the liquid component from the reservoir into the first syringe,
4. Conveying a second part of the liquid component from the reservoir into the second syringe.

11. The method according to claim 10, wherein the system comprises a first port of the plurality of ports and a first conducting means of the plurality of conducting means for fluidically connecting the first port to the reservoir as well as a second port of the plurality of ports and a second conducting means of the plurality of conducting means for fluidically connecting the second port to the reservoir, wherein the first part of the liquid component is conveyed from the reservoir into the first syringe via the first port, and the second part of the liquid component is conveyed from the reservoir into the second syringe via the second port.

12. The method according to claim 11, wherein the reservoir comprises a first compartment and a second compartment, wherein, after the tank has been opened, the first part of the liquid component flows into the first compartment and the second part of the liquid component flows into the second compartment, wherein the first compartment is fluidically connected via the first conducting means to the first port and the second compartment is fluidically connected via the second conducting means to the second port, and the first part of the liquid component is conveyed from the first compartment into the first syringe, and the second part of the liquid component is conveyed from the second compartment into the second syringe.

13. A system for providing a bone cement dough from two starting components comprising an apparatus for providing a liquid component as a first starting component for a bone cement dough from two starting components, comprising a receptacle in which a tank containing the liquid component can be stored, an opening means for opening the tank, a reservoir, fluidically connected to the receptacle, for receiving the liquid component from the tank, at least one port for fluidically connecting the apparatus to a syringe in which a powder component can be stored as a second starting component of the bone cement dough, and at least one conducting means fluidically connecting the reservoir and the at least one port to one another, wherein the tank containing a liquid component as the first starting component is stored in the reputable, and comprising a plurality of syringes, each comprising a power component as the second starting component, wherein the reservoir is divided into a plurality of compartments, and wherein such an amount of liquid component is stored in the tank that, after the tank has been opened, all compartments of the reservoir can be filled with the liquid component and in this case have a fill level that projects at least in sections above a height of the at least one partition wall separating the compartments.

14. The system according to claim 13, wherein the fill level of the compartments projects at least in sections above the height of the partition wall by a maximum of 1 mm.

* * * * *